US010858685B2

(12) United States Patent
Makishima et al.

(10) Patent No.: US 10,858,685 B2
(45) Date of Patent: Dec. 8, 2020

(54) METHOD FOR PRODUCING MODIFIED XYLOPOLYSACCHARIDE

(71) Applicants: B FOOD SCIENCE CO., LTD., Aichi (JP); KIMURA CHEMICAL PLANTS CO., LTD., Hyogo (JP)

(72) Inventors: Satoshi Makishima, Tokyo (JP); Hirofumi Ikeda, Hyogo (JP); Yousuke Yamakawa, Hyogo (JP); Yoshihiko Amano, Nagano (JP); Nobuaki Sato, Nagano (JP); Tsutomu Arai, Nagano (JP)

(73) Assignees: B Food Science Co., Ltd., Aichi (JP); Kimura Chemical Plants Co., Ltd., Hyogo (JP)

( * ) Notice: Subject to any disclaimer, the term of this patent is extended or adjusted under 35 U.S.C. 154(b) by 406 days.

(21) Appl. No.: 15/574,738

(22) PCT Filed: Mar. 28, 2016

(86) PCT No.: PCT/JP2016/059939
§ 371 (c)(1),
(2) Date: Nov. 16, 2017

(87) PCT Pub. No.: WO2016/185801
PCT Pub. Date: Nov. 24, 2016

(65) Prior Publication Data
US 2018/0135088 A1 May 17, 2018

(30) Foreign Application Priority Data

May 18, 2015 (JP) .................................. 2015-100629

(51) Int. Cl.
*C12P 19/14* (2006.01)
*C08B 37/00* (2006.01)
*C08B 37/14* (2006.01)
*B01J 19/18* (2006.01)

(52) U.S. Cl.
CPC .............. *C12P 19/14* (2013.01); *C08B 37/00* (2013.01); *C08B 37/0057* (2013.01); *C08B 37/143* (2013.01); *B01J 19/1806* (2013.01)

(58) Field of Classification Search
CPC ... C12P 19/14; C08B 37/143; C08B 37/0057; B01J 19/1806
USPC ........................................................... 435/99
See application file for complete search history.

(56) References Cited

U.S. PATENT DOCUMENTS 3,679,368 A 7/1972 Balint et al.
6,969,491 B1 11/2005 Marx et al.
2014/0148561 A1 5/2014 Paul et al.

FOREIGN PATENT DOCUMENTS

| CA | 2823101 A1 * | 7/2012 |
|---|---|---|
| CN | 101043937 A | 9/2007 |
| CN | 102864668 A | 1/2013 |
| CN | 103282114 A | 9/2013 |
| EP | 2 471 594 A1 | 7/2012 |
| EP | 3088529 A1 | 11/2016 |
| JP | 2000-054034 | 2/2000 |
| JP | 2003-048901 A | 2/2003 |
| JP | 2008-056599 A | 3/2008 |
| JP | 2009-057354 A | 3/2009 |
| JP | 2010-057509 A | 3/2010 |
| JP | 2011-144336 A | 7/2011 |
| JP | 2013-085523 A | 10/2011 |
| WO | 2014019589 A1 | 2/2014 |
| WO | WO 2014-019589 A1 | 2/2014 |

OTHER PUBLICATIONS

Office Action from Japan Patent Office for JP2015-100629(Japanese, Machine English Translation), dated Jan. 31, 2017.
S. Makishima, M. Mizuno, N. Sato, K. Shinji, M. Suzuki, K. Nozaki, F. Takahashi, T. Kanda and Y. Amano: Development of continuous flow type hydrothermal reactor for hemicellulose fraction recovery from corncob, Bioresource Technology, 100, 2842 (2009).
Office Action from Japan Patent Office received in connection with Japanese Application No. 2015-100629; dated Jan. 31, 2017 (in Japanese and with Machine English Translation).
Office Action from Chinese National Intellectual Property Office (CNIPO) for related Chinese Application No. 201680028880.0, dated May 24, 2019.
Yi, Hong Bao. Construction of Xylanase Engineering Bacteria, First Edition, p. 2, Dec. 31, 2005. Published by Dongbei Linyi University Publishing, China. Machine translation enclosed.
Zhao, Jin Hai. Definition of xylanase. In Biochemical, First Edition, p. 50. China Light Industry Publishing (China), Jan. 31, 2013. Machine translation enclosed.
Extended European Search Report received in connection with European Patent Application No. EP 16796195.2; dated Nov. 6, 2018.
Overend et al., "Fractionation of lignocellulosics by steam-aqueous pretreatments", Royal Soc. of London; Philosophical Transactions, vol. 321, (1987), pp. 523-536.

(Continued)

*Primary Examiner* — Yih-Horng Shiao
(74) *Attorney, Agent, or Firm* — The Marbury Law Group, PLLC

(57) ABSTRACT

Provided is a method for industrially mass-producing a modified xylopolysaccharide from biomass. The biomass used as a raw material includes xylan in plant cell walls, having at least one kind of substituents selected from acetyl, feruloyl arabinofuranosyl and coumaroyl arabinofuranosyl groups in the side chains of xylan. A passage controlling mechanism is internally arranged to generate plug-flow onto a slurry containing the biomass at a solid content in 10 mass % to 30 mass %. The hydrothermal treatment is performed under the controlled conditions: at a temperature of 160° C. or more, at a pressure equal to or higher than the saturated water vapor pressure at said temperature, and with a reaction severity $R_0$ ranging from 3000 to 7000. A modified xylopolysaccharide is obtained as preserving the substituents in the side chains of xylan by performing a continuous hydrothermal treatment in a cylindrical plug-flow reactor.

6 Claims, 10 Drawing Sheets

(56) References Cited

OTHER PUBLICATIONS

Office Action from Chinese National Intellectual Property Office (CNIPO) for related Chinese Application No. 201680028880.0, dated Feb. 3, 2020.
Tian, Zhen, editor. "Ideal Tubular Reactor". In Chemistry Industry Process Safety, published by National Defense Industry Publishing Co., Ltd. (Beijing: Jun. 2007).
Office Action from Chinese National Intellectual Property Office (CNIPO) for related Chinese Application No. 201680028880.0, dated Aug. 19, 2020.
English Translation of Office Action from Chinese National Intellectual Property Office (CNIPO) for related Chinese Application No. 201680028880.0, dated Aug. 19, 2020.
"Optimization of hydrothermal pretreatment of wheat straw for production of bioethanol at low water consumption without addition of chemicals", Mai Østergaard Petersen, Biomass and Bioenergy, 33, pp. 834-840 (2009).

\* cited by examiner

METHOD FOR PRODUCING MODIFIED XYLOPOLYSACCHARIDE

RELATED APPLICATIONS

This application is a national phase entry of international patent application PCT/JP2016/059939 filed Mar. 28, 2016, which claims benefit of priority to Japanese Application Serial No. 2015-100629, filed May 18, 2015, the entire disclosures of which are incorporated herein by reference in their entireties.

FIELD OF INVENTION

The present invention relates to a method for producing a modified xylopolysaccharide.

BACKGROUND ART

According to the Japanese dietary intake standard of dietary fibers described in the Ministry of Health, Labor and Wealth Plan of 2015 edition, it is said that preferably male and female adults take in dietary fibers of 19 g-20 g or more, and 17 g-18 g or more per day, respectively. However, according to the Survey Report of Public Health and Nutrition of 2012 edition, the fact is that male and female adults take in dietary fibers of only about 13.0 g-17.1 g, and about 13.2 g-17.1 g, respectively.

A market of polysaccharides such as indigestible dextrin, polydextrose and glucomannan that are a class of dietary fibers has a tendency to be expanding. This tendency shows high interests of the people in dietary fibers, and therefore the market has exceeded the oligosaccharide market in size.

On the other hand, there are movements in the oligosaccharide market not only to pursue a goal for improving an intestine function simply shown as a growth factor of bifidobacteria but also to demand new functions for ameliorating allergic symptoms and improving an immune function to the oligosaccharide.

Originally, dietary fibers in many cases refer to a general term of partial hydrolysates of cellulose, hemicelluloses and lignin constructing plant cell walls, in addition to those substances themselves. However, plant cell walls are hard to be degradable, causing difficulty in industrially extracting dietary fibers from plant cell walls at low cost. This extraction has a technical problem the same as the difficulty in industrially producing bioethanol from a cellulosic material. Hence, water soluble dietary fibers actually sold in the market are in many cases indigestible polysaccharides produced from starch as a starting material.

Xylan, which is a kind of hemicelluloses constructing plant cell walls, is a polymer having β-D-xylopyranose as a basic unit. Further, a technology for producing xylose and a xylooligosaccharide from xylan has already been put into practical use (see Patent Document 1). However, in view of a nutrient tendency of modern people, demanded is a technology for separating a macromolecular polysaccharide having a function of dietary fibers, or a technology for collecting a functional oligosaccharide having modified side chains derived from plant cell walls.

A method for producing a saccharide from biomass containing xylan is known from old days, which is performed by hydrolyzing xylan via using an acid or an alkali. Specifically, xylose (i.e., monosaccharide) which is a raw material of xylitol is industrially obtained by hydrolyzing xylan by sulfuric acid. Further, it is known that a method for producing an oligosaccharide from xylan is performed by enzymatically hydrolyzing xylan. Commercially available xylooligosaccharides are in many cases produced by such an enzymatic method. The enzymatic method is performed following a pretreatment of adding an alkaline solution in advance or boiling a raw material from the viewpoint of shortening a reaction time.

The respective technologies as mentioned above for producing a saccharide have a variety of disadvantages. That is, although hydrolysis proceeds by an acid-base catalyst, an environmental load caused by an acid and an alkali is relatively large and a useful group derived from plant cell walls that modifies a xylopolysaccharide is removed by an acid and an alkali. Therefore, recently a so-called hydrothermal reaction technology is attracted an attention, in which high-temperature and high-pressure water is utilized to biomass (see Patent Document 2 and Non-Patent Document 1).

When the temperature and pressure of water exceed the critical point of 374° C. and 23.4 Mpa, the water becomes a homogeneous fluid different from a gas or a liquid. Such a fluid is called supercritical water and shows high reactivity enough to decompose almost organic substances. Note, a fluid kept at a lower temperature and pressure than the critical point is called subcritical water, high-temperature and high-pressure water, or pressurized hot water or the like.

A hydrolysis reaction of a saccharide chain caused when an acid, an alkali and an enzyme are used proceeds by an acid-base catalyst. Herein, high-temperature and high-pressure water in the hydrothermal reaction technology has the same function. Water provides a variety of reaction fields when a temperature and a pressure thereof are changed. This profile allows the high-temperature and high-pressure water to be assessed as a solvent with a low environmental load so that polysaccharides constructing plant cell walls are hydrolyzed and made soluble in the high-temperature and high-pressure water.

A hydrothermal reactor experimentally generating high-temperature and high-pressure water is configured to include a batch type pressure container and a temperature controller made of an anticorrosive metal with a capacity of several to several tens mL. Further, a continuous flow type hydrothermal reactor having a tube type of reaction pipe is also investigated. Those hydrothermal reactors are verified in a bench plant scale.

In a continuous flow type hydrothermal reactor, a reaction pipe having a certain degree of a heat capacity and a pipe length is subjected to temperature control, and a biomass material passes therethrough at a constant rate. Further, those hydrothermal reactors have an advantage for allowing a sharp reaction temperature and time to be achieved via setting appropriate conditions to the temperature rising and cooling steps (see Patent Document 3 and Non-Patent Document 2).

DOCUMENTS OF PRIOR ART

Patent Documents

Patent Document 1: Japanese Unexamined Patent Application Publication No. 2003-48901.

Patent Document 2: Japanese Unexamined Patent Application Publication No. 2010-57509.

Non-Patent Document

Non-Patent Document 1: S. Makishima, M. Mizuno, N. Sato, K. Shinji, M. Suzuki, K. Nozaki, F. Takahashi, T.

Kanda and Y. Amano: Development of continuous flow type hydrothermal reactor for hemicellulose fraction recovery from corncob, Bioresource Technology, 100, 2842 (2009).

SUMMARY OF INVENTION

Problems to be Solved by Invention

A method for producing xylose (i.e., monosaccharide) by decomposing biomass containing xylan into low molecules may be conducted by using an acidic hydrolysis method, for example, by using an acid to conduct a hydrolysis treatment. However, the acidic hydrolysis method has high reactivity so that hydrolysis of xylan proceeds too rapidly.

This reactivity makes it difficult to terminate the hydrolysis reaction within a stage of xylopolysaccharide having a large molecular weight (i.e., the xylopolysaccharide includes a xylooligosaccharide having about 2-12 polymerization degree of monosaccharide (i.e., degree of polymerization), the same will be applied hereinafter).

Further, from the viewpoint of the high hydrolysis rate and selectivity, it is likely that xylan in biomass is hydrolyzed via applying an enzyme (e.g., xylanase) capable of hydrolyzing xylan to biomass. However, if biomass is treated by an alkali as a pretreatment of the enzymatic reaction, this treatment hydrolyzes substituents such as an acetyl group and an arabinofuranosyl group or the like derived from plant cell walls and present on the side chains of xylopolysaccharide in xylan.

Accordingly, in a method for using an alkali combined with an enzyme, predominantly produced is a low molecular and unmodified xylo-homo-oligosaccharide having no side chains (i.e., degree of polymerization is 2-3). This makes it difficult to collect a modified xylopolysaccharide.

Here, from the viewpoint of protecting the modified side chains of a xylopolysaccharide against an alkali treatment, there is a method for directly making xylanase act on biomass without an alkali treatment. However, in this case, the hydrolysis rate becomes extremely low so that the modified side chains inhibit the reaction, resulting in a decrease in yield. Therefore, in view of increasing the hydrolysis rate, it is considered to use a large amount of xylanase.

However, a commercially available xylanase formulation is contaminated with esterase during the production process. Thus, use of a large amount of xylanase allows contamination of a large amount of esterase in the reaction system. This contaminated esterase removes the substituents present in the xylan side chains so that a low molecular and unmodified xylo-homo-oligosaccharide is predominantly formed similarly to the method for using an alkali in combination with an enzyme. This makes it difficult to collect a modified xylopolysaccharide.

When the above disadvantages are taken into consideration, it is difficult to selectively and industrially produce a modified xylopolysaccharide with a large molecular weight by an enzymatic method. Further, production of a low molecular modified xylopolysaccharide requires a large amount of purified xylanase from which esterase is removed, which results in an industrially unpractical process. Therefore, demanded is a method for industrially mass-producing a modified xylopolysaccharide.

Herein, there is possibility of preferentially producing a modified xylopolysaccharide if a hydrothermal reaction of biomass containing xylan can be preferably controlled. In the hydrothermal reaction, a water molecule reacts with xylan as a nucleophilic agent. As a result, a β-1,4-bond between xyloses, which are polysaccharides mainly constructing xylan, is preferentially hydrolyzed, and therefore a modified xylopolysaccharide is obtained by protecting substituents. Hence, there is possibility of industrially mass-producing a modified xylopolysaccharide.

So far, in the research using a batch type hydrothermal reactor, a reactor with a capacity of several to several tens ml has been utilized. In a scale-up trial for industrial production using a batch capacity over 1 L, amounts of time more than several tens minutes to 1 hour may be consumed until the reaction temperature reaches a preset temperature to be stably kept, if a sample material is subjected to the reaction conditions, for example, at 200° C. and for 10 min. Even though a heat capacity of heater, temperature control and agitation ability inside the reactor are improved, it is difficult to uniformly control the energy of the hydrothermal reaction inside the batch merely within 10 minutes against the predominant heat histories generated in the heating and cooling steps. Excessive heat histories not only cause a removal of substituents but also increase the amounts of monosaccharide xylose thus generated. This results in production of furfural that is an excessive degradation product of xylose. Since furfural strongly inhibits the enzymatic reaction and purification steps performed in a late stage, a side reaction generating furfural has to be inhibited.

Hence, a continuous flow type hydrothermal reactor provided with a tube type reaction pipe has been developed. The reactor is principally configured to make a biomass slurry flow into the thermo-controlled reaction pipe at a constant rate. Therefore, if components of the heating and cooling units are well designed, this may afford a merit so that extremely sharp reaction temperature and time may be achieved (e.g., Japanese Unexamined Application Publication No. 2008-253861 and "S. Makishima and N. Sato: Production technology of various saccharides using hydrothermal reaction, Applied Saccharide Science, 2 (3), pp. 174-179 (2012)).

However, such a tube type reactor also causes a scale-up problem similarly to the above batch type reactor. For example, as a cross-sectional area of a tube with a diameter of one inch is increased for improving the treating performance of the tube type reactor, movements of a fluid inside the reactor gradually change.

Specifically, as the cross-sectional area of the tube increases, the efficiency of heat conductivity to a raw material is decreased. Further, such phenomena may be happened as turbulence occurs inside the reactor to let a raw material pass through more rapidly than expected (i.e., abnormal passing through), or as accumulation is caused via sedimentation leading to delay of the flow.

As mentioned above, a merely increase in the cross-sectional area of the tube type reactor deteriorates a so-called "plug-flow" condition in which a raw material thus flowed into the reactor is successively discharged by receiving uniform reaction energy. Further, such a deteriorated phenomenon remarkably decreases a yield of the modified xylopolysaccharide, leading to generation of by-products.

For solving the above drawbacks, it may be considered that a plurality of tube type reactors are connected in parallel and a large pump is connected so as to make a raw material flow through the heated tube type reactors respectively. However, even though a total amount of the distributions is increased, a flow rate per tube type reactor fluctuates due to a difference in a pressure loss of each tube type reactor.

Accordingly, this results in a deflection of reaction histories. Therefore, from the viewpoint of avoiding the deflection, the tube type reactor and the large pump have to be independently designed. However, this design requires parallel arrangement of several hundreds of tube type reactors with a low-capacity, resulting in requirement for huge device costs.

Researching a high-temperature and high-pressure fluid is nothing less than applying physicochemical properties of a medium like water, and therefore has been investigated in various chemical engineering fields such as process engineering, material engineering and nuclear engineering. In many cases, a reactor generating a hydrothermal reaction is designed almost directed to complete hydrolytic decomposition of organic compounds or a pre-treatment device of fermenting biomass or enzymatically saccharifying biomass (e.g., Japanese Patent Publication No. 4691214).

The present invention is made from the viewpoint of solving the above drawbacks. Thus, an object of the present invention is to provide a method capable of industrially mass-producing a modified xylopolysaccharide from biomass.

Means for Solving Problems

The present inventors have earnestly investigated to solve the above drawbacks, which results in the following findings. Namely, the present invention relates to a method for producing a modified xylopolysaccharide which preserves substituents on a side chain of xylan. A raw material of the method is biomass containing xylan in plant cell walls to produce the modified xylopolysaccharide. Herein, xylan has at least one kind of substituents selected from an acetyl group, a feruloyl arabinofuranosyl group and a coumaroyl arabinofuranosyl group, on a side chain thereof.

Specifically, the biomass is subjected to a continuous hydrothermal treatment under controlled conditions: at a reaction temperature of 160° C. or more; at a reaction pressure of saturated water vapor pressure or more at said reaction temperature; and with a severity parameter $R_0$ ranging from 3000 to 7000 calculated by the following equation (1). The continuous hydrothermal treatment is conducted by a cylindrical plug-flow reactor provided with a passage controlling mechanism inside the reactor. The passage controlling mechanism generates plug-flow onto the slurry including the biomass in a solid content at the ratio of 10 mass % to 30 mass %.

$$R_o = \int_0^t \exp\left(\frac{T(t) - T_r}{\omega}\right) dt \quad \text{Equation (1)}$$

where T(t) represents a time variation in temperature (° C.); Tr represents a standard temperature (100° C.); t represents a time (min); ω represents a constant (=14.75).

According to the above method, generation of xylose and an excessive degradation product thereof furfural can be suppressed, and a modified xylopolysaccharide that preserves a side chain structure derived from plant cell walls can be produced.

Further, the passage controlling mechanism is preferably configured to include a columnar rotator that is rotatable around a center axis arranged in the direction parallel to a flow of the slurry.

The passage controlling mechanism further includes a plurality of passage controlling blades consisting of a plate member arranged on a side surface of the rotator, directed to the outside of the rotator and extended to the direction of the slurry flow.

The above passage controlling mechanism may generate sufficient plug-flow inside the reactor, and suppress side-reactions due to a constantly kept severity parameter affecting a raw material, whereby a modified xylopolysaccharide can be produced without a decrease in a yield despite of an increase in the production scale.

Further, preferably a distance between the passage controlling blade facing the inner wall of the plug-flow reactor and said inner wall may be set to 5 mm or less.

The distance may prevent sedimentation and retention of the slurry, and occurrence of abnormal passage thereof.

Further, preferably the rotator may pivot so that a circumferential speed of the plate member is in the range from 0.02 m/sec to 0.3 m/sec.

This range of the speed may elongate a migration pathway of the slurry, allowing prevention of the abnormal passage and sedimentation of the slurry as well as the excessive retention thereof. Further, the thermal conductive efficiency may be also improved. As a result, the plug-flow reactor may be designed in a compact size.

Moreover, preferably a through hole may be formed in the plate member so that the slurry can pass therethrough in a circumferential direction of the rotator.

This structure may generate mild and complicated passages inside the reactor, enabling the plug-flow to be realized without disturbing a flow of the slurry, leading to a more increase in the yield.

Further, preferably a scraper that is rotatable around a peripheral part of the plate member as a pivot center is arranged, and the scraper contacts with an inner wall of the plug-flow reactor while the rotator is pivoting.

The structure may prevent the retention of the slurry and adhesion of foreign materials (i.e., burning) near the inner wall inside the reactor. Thus, highly accurate plug-flow may be realized without affected by a property of the raw material slurry and a scale of the device.

Moreover, at least either purified β-xylosidase or xylanase is made to react with a solubilized modified xylopolysaccharide in the plug-flow reactor. This reaction may preserve a substituent on a side chain of the modified xylopolysaccharide, allowing modified xylooligosaccharides to be produced.

As mentioned above, for example, highly acetylated xylooligosaccharides (e.g., mono-, di-, tri-, tetra- or penta-acetyl-xylooligosaccharide) and monosaccharide xylose may be collected in a short reaction time, while leaving an acetyl group derived from plant cell walls to be preserved on a side chain. Additionally, for example, highly acetylated xylooligosaccharides (e.g., mono-, di-, tri-, tetra-, or penta-acetyl-xylooligosaccharide), feruloyl-α-L-arabinofuranosyl-xylooligosaccharide (FA-XOS) and p-coumaroyl-α-L-arabinofuranosyl-xylooligosaccharide (CA-XOS) may be collected. Besides those oligosaccharides, modified xylooligosaccharides having the above described substituents such as mono-, di- or tri-acetyl-FA-XOS and mono-, di- or tri-acetyl-CA-XOS may be further collected.

Effect of Invention

According to the present invention, a method for industrially mass-producing a modified xylopolysaccharide from biomass may be provided.

BRIEF DESCRIPTION OF DRAWINGS

FIG. 3A is a cross-sectional diagram when viewed in the direction vertical to the slurry flow. FIG. 3B is a cross-sectional view taken along the line A-A of FIG. 3A.

FIG. 4A is a cross-sectional diagram when viewed in the direction vertical to the slurry flow. FIG. 4B is a cross-sectional view taken along the line B-B of FIG. 4A.

EMBODIMENTS FOR CARRYING OUT INVENTION

Hereinafter, aspects (or embodiments) for carrying out the present invention will be described in detail appropriately referring to attached drawings. Note, a "modified xylopolysaccharide" is a polysaccharide comprised of glycoside bonded xyloses (i.e., xylopolysaccharide). The modified xylopolysaccharide represents a polysaccharide in which substituents (e.g., acetyl group) are present on the side chains thereof.

Further, in the present embodiment, plug-flow is an extruded flow so that a slurry is made to flow in the same distribution of velocity inside a reactor 12. Specifically, in a plug-flow reactor, sub-layers of the flowing slurry are prevented from being mixed, and abnormal passage and retention of the slurry are prevented, allowing the slurry to flow at a constant velocity.

Therefore, the slurry fed to the reactor 12 is successively extruded without remaining inside the reactor 12, thereby to be discharged from the reactor 12. This feature allows all of the slurry to be uniformly heated in the reactor 12 without exception, and a hydrothermal reaction to be performed under uniform conditions, thereby producing a modified xylopolysaccharide.

Here, the term of "plug-flow" in the present embodiment means that substantial plug flow (i.e., plug flow condition, plug flow state) is generated all over inside the reactor 12. Herein, partial turbulence and retention of the slurry flow may be generated as long as such partial turbulence and retention do not significantly deteriorate a yield curve of the modified xylopolysaccharide. Therefore, needless to say, the "plug-flow" in the present embodiment may be a theoretical and ideal "plug flow" generating no turbulence and retention of the slurry flow, but it is not limited to the theoretical and ideal "plug flow".

<Equipment Structure of Reaction System 100>

Figure 1:
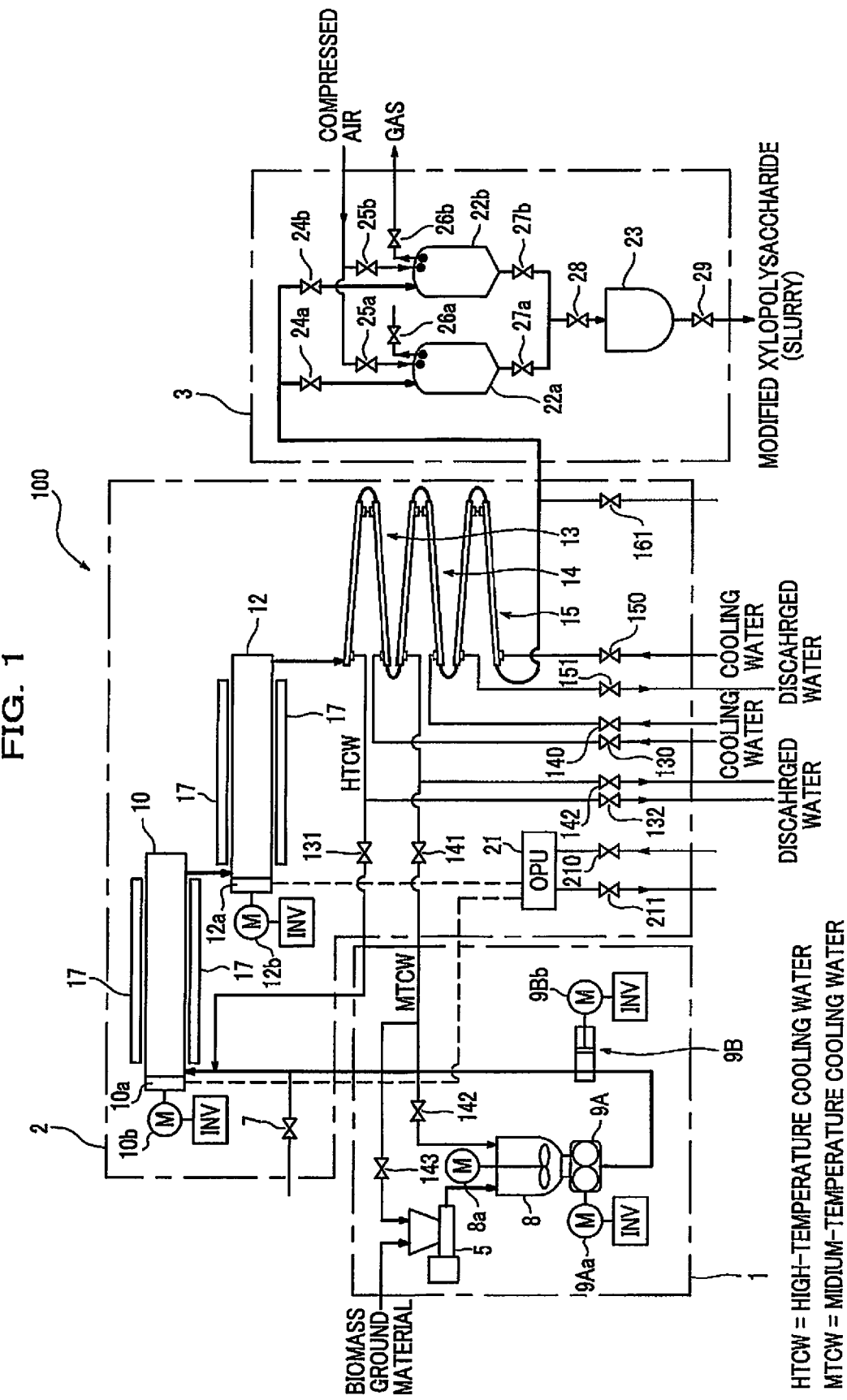
FIG. 1 is a system diagram showing a reaction system of the present embodiment.
Figure 2:
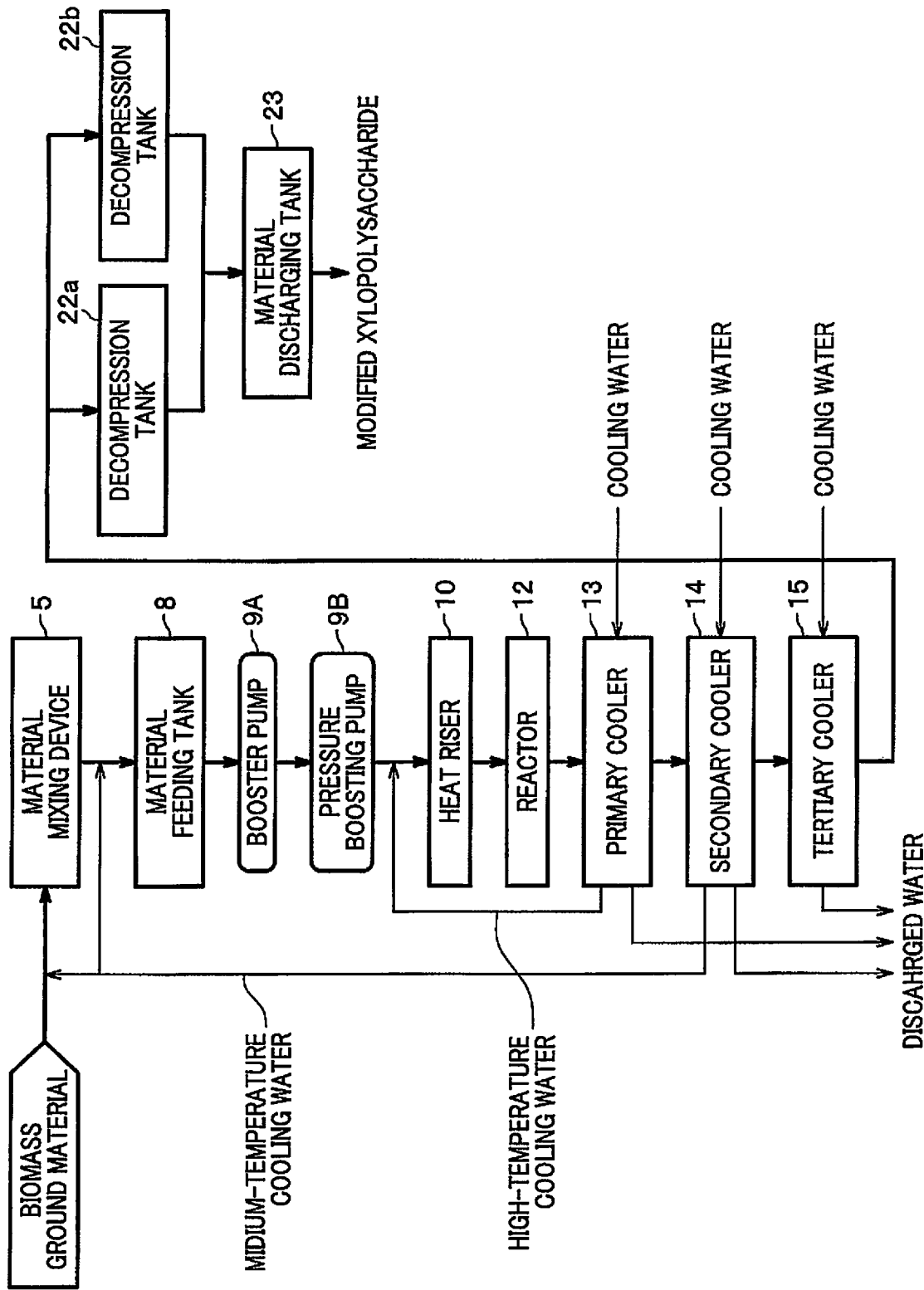
FIG. 2 is a block diagram showing the respective devices used for producing a modified xylopolysaccharide from a biomass ground material in the reaction system of the present embodiment.

FIG. 1 is a system diagram showing a reaction system 100 in the present embodiment. Further, FIG. 2 is a block diagram showing the respective devices used for obtaining a modified xylopolysaccharide from a biomass ground material in the reaction system 100 of the present embodiment. The reference numerals shown in FIG. 2 are identical to those in FIG. 1.

In the reaction system 100, a modified xylopolysaccharide which preserves substituents can be obtained as a hydrolysis product of xylan from a raw material biomass containing xylan in plant cell walls. Herein, xylan has at least one kind of substituents selected from an acetyl group, a feruloyl arabinofuranosyl group and a coumaroyl arabinofuranosyl group on the side chains thereof. The modified xylopolysaccharide is produced in the reactor 12. Accordingly, the modified xylopolysaccharide may be produced particularly by the reactor 12 while preventing generation of xylose and the excessive decomposition product of xylose: furfural.

Biomass used in the reaction system 100 is, for example, derived from plants such as a corncob which is available as an agricultural by-product in relatively large amounts, and contains xylan in the plant cell walls thereof. Large amounts of xylan are also contained in plant cell walls of food processing residues of agricultural products such as a corncob and sugarcane bagasse, and soft biomass such as sorghum and erianthus. Further, large amounts of xylan are contained in wood-based plant cell walls of a broad-leaved tree and a pulpwood.

The reaction system 100 includes a material feeding unit 1, a reactor 2 and a material discharging unit 3. The material feeding unit 1 supplies a biomass ground material to the reactor 2, in which the biomass ground material is to be used as a raw material of a modified xylopolysaccharide. The reactor 2 produces the modified xylopolysaccharide from a slurry containing the biomass ground material thus fed to the material feeding unit 1. The material discharging unit 3 discharges the xylopolysaccharide thus produced.

Hereinafter, structures of the respective devices will be described in detail following a processing flow of the materials beginning from the biomass ground material fed to the material feeding unit 1 to the production of the modified xylopolysaccharide discharged from the material discharging unit 3.

The material feeding unit 1 is configured to include a material mixing device 5 and a material feeding tank 8. First, the biomass ground material is supplied to the material mixing device 5. A size of the biomass ground material fed to the material feeding unit 1 is preferably 5 μm or more as a mean particle diameter, more preferably 20 μm or more, further more preferably 30 μm or more. An upper limit thereof is preferably 1000 µm or less, more preferably 60 µm or less, further more preferably 40 µm or less.

The mean particle diameter is measured by a laser diffraction scattering type particle diameter measuring device (Nikkiso Co., Ltd.: MT3300). In the material mixing device 5, the biomass ground material is mixed with middle-temperature cooling water (ca. 100° C. or less) from a cooler 14 to be described later, thereby to form a fluid slurry. Supply of the medium-temperature cooling water from the cooler 14 is controlled by opening/closing operation of a valve 143. Then, the slurry thus formed is introduced into a material feeding tank 8.

The material feeding tank 8 is provided with a thermostat and stirring blades used for preventing sedimentation. Due to those parts, the slurry is stored in the material feeding tank 8 under stirring while appropriately keeping a temperature thereof. Note, the stirring blades are controlled by an inverter controlled motor 8a. As described later medium-temperature cooling water (ca. 100° C.) fed from a cooler 14 is supplied into the material feeding tank 8, while details of which will be described later.

The materials stored in the material feeding tank 8 are supplied to the reactor 2 after a flow rate thereof is controlled by a pair of pumps: a booster pump 9A used for extruding the material and a pressure boosting pump 9B. The booster pump 9A is driven by an inverter controlled motor 9Aa. Further, the pressure boosting pump 9B is driven by an inverter controlled motor 9Ba.

Here, a part of the materials stored in the material feeding tank 8 is discharged outside by opening/closing of a valve 7. Further, besides the material stored in the material feeding tank 8, high-temperature cooling water (ca. 120° C.-180° C.) fed from a cooler 13 as described later is supplied into the reactor 2, while details of which will be described later.

The reactor 2 is configured to include a tubular type heat riser 10 that raises a temperature of a slurry, a cylindrical reactor 12 that produces a modified xylopolysaccharide from xylan (i.e., having a substituent in molecular chains) in the slurry, a heater 17 that heats the insides of the heat riser 10 and the reactor 12, and 3-stage coolers (i.e., primary cooler 13, secondary cooler 14 and tertiary cooler 15). When a slurry is supplied to the heat riser 10, the slurry mixed with high-temperature cooling water (ca. 120° C.-o 180° C.) flowing from the reactor 12 described later is supplied to the heat riser 10. This construction improves the thermal efficiency of the reaction system 100.

Here, a calorific value by the heater 17 and feed quantity of the high-temperature cooling water are feedback-controlled based on temperatures measured by temperature sensors (not shown) arranged in the heat riser 10 and the reactor 12.

In the heat riser 10 and the reactor 12, a hydrothermal reaction is conducted while generating plug-flow of the slurry successively passing through the insides thereof. The details will be described later referring to FIG. 2. Further, the heat riser 10 and the reactor 12 have the same structure. Herein, the structure will be explained as exemplifying the reactor 12. Inside the reactor, a shaft 19 (see FIGS. 3A and B; not shown in FIGS. 1 and 2) is arranged. The shaft 19 is connected to an inverter-controlled motor 12b. Note, in the present embodiment, the heat riser 10 and the reactor 12 are independently arranged. However, the arrangement of the heat riser 10 may be omitted by making the reactor 12 take over the function of the heat riser 10.

Further, a disk-shaped disk member 12a used for sealing the inside of the reactor 12 is attached to an end of the reactor 12. The shaft 19 connected to the motor 12b is arranged near the center of the disk member 12 so that the shaft 19 passes through the inside and outside of the reactor 12. At the disk member 12, an oil pressure unit 21 secures the sealing performance of a shaft seal 12c arranged at a sliding portion of the shaft 19 which passes through the reactor 12. Note, cooling water is fed to the oil pressure unit 21 so as to cool the heat generated by hydraulic operation. Circulation of the cooling water is controlled by opening/closing of valves 210 and 211. The inside structures of the heat riser 10 and the reactor 12 will be described later referring to FIG. 2 and so on.

A slurry is rapidly heated up to about 200° C. that is a preset temperature of the hydrothermal reaction in the heat riser 10. Then, the slurry thus heated is fed to the reactor 12, so that a formation reaction (i.e., hydrothermal reaction under the plug-flow condition) of a modified xylopolysaccharide is performed for a predetermined time in the reactor 12.

The slurry treated in the heat riser 10 and the reactor 12 circulates through the primary cooler 13, the secondary cooler 14 and the tertiary cooler 15 in this order, thereby being cooled down to about 40° C. or less. Note, in the following descriptions, "a primary cooler 13" is simply referred to as "a cooler 13, "a secondary cooler 14" is simply referred to as "a cooler 14, and "a tertiary cooler 15" is simply referred to as "a cooler 15, for simplifying the descriptions.

The slurry thus cooled to about 40° C. or less in the coolers 13, 14 and 15 is supplied to the material discharging unit 3. Note, a part of the cooled slurry is discharged outside through a valve 161, and the rest is supplied to the material discharging unit 3.

All of those coolers 13, 14 and 15 are heat exchangers configured by a double pipe (not shown). Cooling water is supplied to the coolers 13, 14 and 15 from independent routs so that cooling water is circulated through the coolers respectively. More specifically, cooling water of which circulation is controlled by a valve 130 is supplied to the cooler 13. Cooling water of which circulation is controlled by a valve 140 is supplied to the cooler 14. Further, cooling water of which circulation is controlled by a valve 150 is supplied to the cooler 15.

Further, heat exchange with the slurry results in production of heated water (i.e., used cooling water), and different kinds of cooling water having different temperatures are discharged from the 3-stage coolers 13, 14 and 15 respectively. Thus, the slurry supplied to the upper-stage cooler 13 has a high temperature. Thereby, used cooling water discharged from the cooler 13 (i.e., high-temperature cooling water) has the highest temperature. Accordingly, as mentioned above, the high-temperature cooling water is supplied to the slurry that is to be supplied to the heat riser 10.

At that time, the high-temperature cooling water is supplied by closing a valve 132. In contrast, when the high-temperature cooling water is not supplied to the slurry, the high-temperature cooling water is discharged outside by opening the valve 132.

Moreover, used cooling water discharged from the middle-stage cooler 14 (i.e., medium-temperature cooling water) is supplied to the material mixing device 5 and the material feeding tank 8 as mentioned hereinbefore.

At that time, when the medium-temperature cooling water is supplied to the material mixing device 5 and the material feeding tank 8, the cooling water is supplied by opening a valve 141 under the condition that a valve 142 is closed.

In contrast, when the medium-temperature cooling water is not supplied to the material mixing device 5 and the material feeding device 8, the medium-temperature cooling water is discharged outside by opening the valve 142 under the condition that the valve 141 is closed.

Furthermore, used cooling water discharged from the late-stage cooler 15 (i.e., low-temperature cooling water) is discharged outside by opening a valve 151.

Here, the high-temperature cooling water and the low-temperature cooling water are supplied from the coolers 13, 14 and 15 so that a solid content concentration of the slurry which is to be supplied to the reactor 12 is in the range from 10 mass % to 30 mass %.

The material discharging unit 3 is configured to include parallel decompression tanks 22a and 22b, and a material discharging tank 23 and so on. The decompression tanks 22a and 22b are used for releasing a pressure of the slurry (i.e., pressurized slurry) discharged from the reactor 2, and discharging the slurry into an environment under atmospheric pressure. The decompression tanks 22a and 22b are connected with material switching valves 24a, 24b, 27a and 27b; compression air valves 25a and 25b; vent valves 26a, 26b; a pressure sealing valve 27; and a material discharging valve 29, respectively.

When those components are controlled together, the slurry is stored in the decompression tanks 22a and 22b while keeping the air pressure inside the reactor 12 by compression air.

More specifically, the operation is controlled so that the slurry from the reactor 2 is fed through the material switching valve 24a to the decompression tank 22a, and the air pressure of the decompression tank 22a becomes equal to the pressure of the reactor 12 by the vent valve 26. At that time, all of other valves in the material discharging unit 3 are closed.

Under the above conditions, when the decompression tank 22a is filled with the slurry, the material switching valve 24a is made to be closed and the material switching valve 24b and the vent valve 26b are made to be opened. The slurry from the reactor is fed through the material switching valve 24b to the decompression tank 22b. The operation is controlled so that the air pressure of the decompression tank 22b becomes equal to the pressure of the rector 12 by the vent valve 26b.

On the other hand, the compression tank 22a filled with the slurry is controlled to discharge the slurry outside. More specifically, first, the vent valve 26a connected to the decompression tank 22a is gradually opened, whereby gas inside the decompression tank 22a is discharged outside. As a result, the pressure inside the decompression tank 22a is lowered down to a pressure level at which the slurry can be discharged. Then, when the pressure inside the decompression tank 22a is lowered, the discharging valve 27a and a flow rate adjusting valve 28 are made to be opened. The slurry inside the tank 22a is fed to the material discharging tank 23. As a result, the slurry thus fed to the material discharging tank 23 is stored in the material discharging tank 23.

When all of the slurry inside the decompression tank 22a is fed to the material discharging tank 23, the flow rate adjusting valve 28 and the material discharging valve 27a are made to be closed, and the compression air valve 25a is made opened thereby to feed compression air into the compression tank 22a. Then, when the pressure inside the decompression tank 22a and the pressure inside the reactor 12 become equal, the compression air valve 25a is made to be closed to enter a standby state.

Next, the slurry inside the compression tank 22b is fed to the material discharging tank 23 similarly to the compression tank 22a. As mentioned above, the steps of discharging the slurry from the decompression discharging tank 22a and discharging the slurry from the decompression discharging tank 22b are performed alternately, so that all of the slurry is supplied to the material discharging tank 23 while keeping the internal pressure of the reactor 12. Accordingly, the slurry including a modified xylopolysaccharide is discharged from the material discharging tank 23 by opening the material discharging valve 29.

As mentioned above, the internal pressure of the reactor 12 is kept, which allows the hydrothermal reaction to be more surely performed in the reactor 12, thereby to yield a modified xylopolysaccharide. Further, the material discharging unit 3 can be a flow type unit, in addition to the flow type reactor 12. This can make the whole of the reaction system 100 be a complete flow type system.

<Structure of Reactor 12>

Figure 3B:
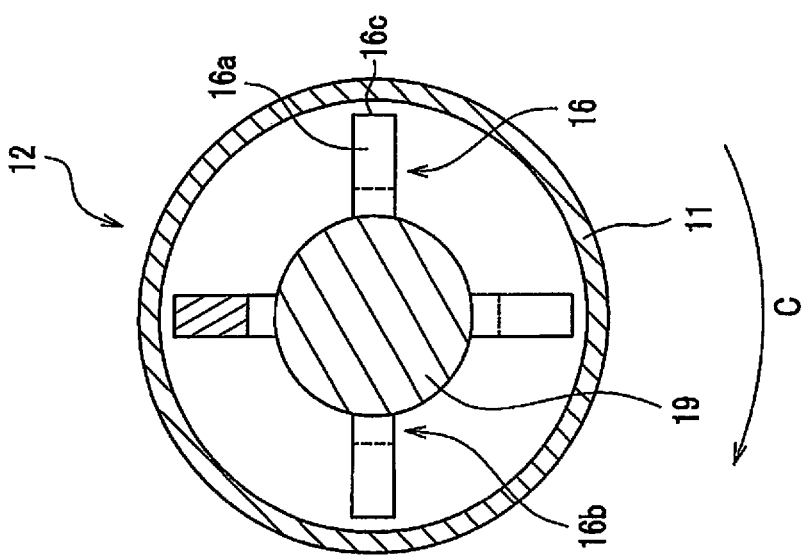
FIGS. 3A and 3B are diagrams showing inner structures of the reactor arranged in the reaction system of the present embodiment.
Figure 3A:
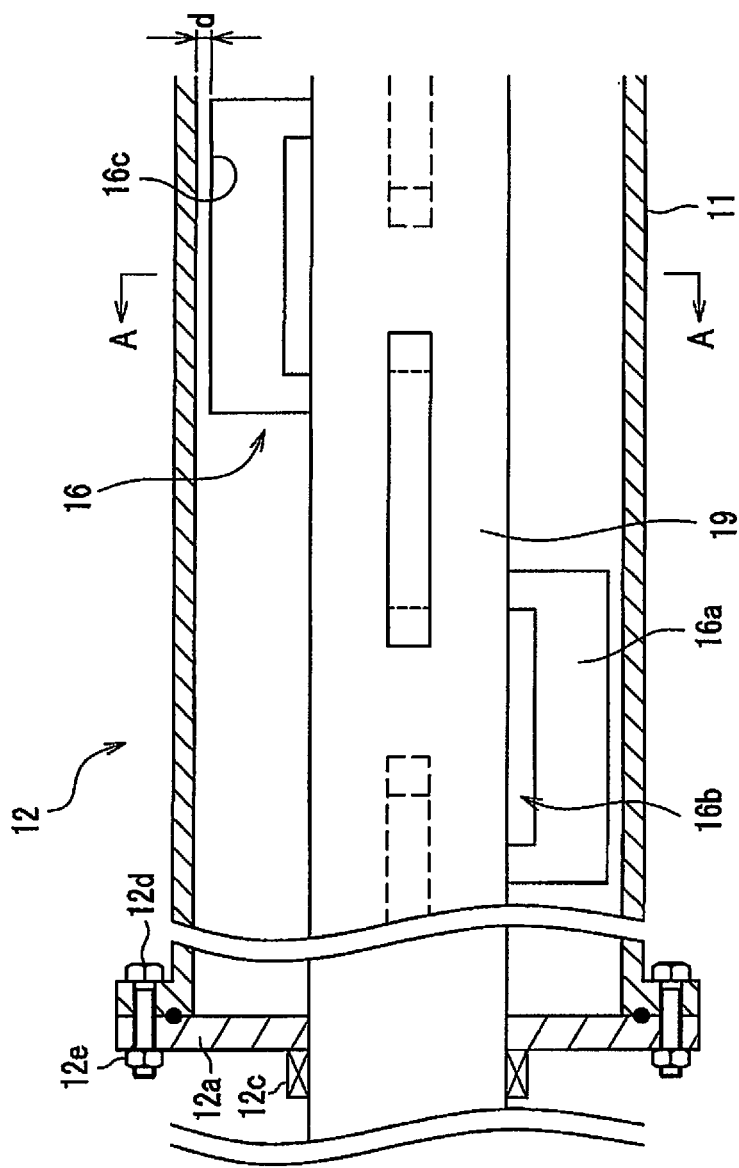

FIGS. 3A and 3B are diagrams showing the internal structure of the reactor 12 arranged in the reaction system of the present embodiment. FIG. 3A is a cross-sectional diagram when viewed in the direction vertical to the flow direction of the slurry. FIG. 3B is a cross-sectional view taken along the line A-A of FIG. 3A. Note, the reactor 12 shown in FIGS. 3A and 3B is merely an example of a device usable for operating a collecting system 100 of the present embodiment. Thus, as long as the reactor is a cylindrical plug-flow reactor including a passage controlling mechanism that generates plug-flow inside the reactor, any reactors may be utilized therefor. Note, as mentioned above, since the internal structure of the heat riser 10 is the same as in FIGS. 3A and 3B, in the following descriptions, the internal structure of the reactor 12 will be only explained to omit the duplicate explanations.

As shown in FIGS. 3A and 3B, the reactor 12 is configured to include a hollow pipe (or cylinder) 11; a columnar shaft 19 arranged inside the pipe 11 and rotating on a center pivot parallel to the direction of the slurry flow; and passage controlling blades arranged at the external surface of the shaft 19. Further, the shaft 19 is connected to a motor 12b as mentioned before. This construction enables rotation of the shaft 19 and the passage controlling blades 16 associated with movement of the motor 12b. The rotation direction is shown as an arrow C in FIG. 3B. However, the direction may be the reverse one.

Further, the end of the pipe 11 (i.e., end in the left direction of the drawing) is releasable. However, when the reactor 12 is operated, the inside of the pipe is sealed by the disk member 12a as mentioned before. The disk member 12a is fastened to a flange part of the pipe 11 by using bolts 12d and nuts 12e. An O-ring is arranged between the disk member 12a and the flange part. Further, a shaft seal 12c is arranged at the outside of the disk member 12 to seal the disk member 12a and the shaft 19.

The passage controlling blade 16 is configured to control a passage of a slurry (or flowing of a slurry) inside the reactor 12. In the present embodiment, the slurry is uniformly heated by the rotation of the shaft 19 having the passage controlling blades 16. Therefore, those parts (or passage controlling mechanism as described before) may be called "uniformly heating means". The plurality of passage controlling blades 16 are arranged on a circumferential surface of the shaft 19. In the reactor 12, especially the plurality of passage controlling blades 16 are arranged extending to four directions with 90° intervals in the cross-sectional view shown in FIG. 3B.

This construction enables generation of the sufficient plug-flow inside the reactor 12. Further, side-reactions are prevented because the severity parameter affecting the raw material is constantly held, whereby a modified xylopolysaccharide may be obtained without a decrease in the yield despite of an increase in the production scale.

The passage controlling blade 16 is formed by the plate member 16a directed outward from the shaft 19 and extending in the direction parallel to the slurry flow. The plate member 16a may have a thickness, for example, in the range from 3 mm to 15 mm. Further, the passage controlling blade 16 (i.e., plate member 16a) arranged on a side surface of the shaft 19 may have a width (i.e., length in the direction of the slurry flow), for example, in the range from 50 mm to 150 mm.

The reactor 12 has the following dimensions. The pipe 11 may have an inner diameter, for example, in the range from 50 mm to 300 mm. Further, the reactor 12 may have a length (i.e., length in the flowing direction), for example, ranging from 500 mm to 3000 mm. Moreover, the shaft 19 arranged inside the reactor 12 may have a diameter, for example, ranging from 30 mm to 200 mm.

Conventionally, a reactor having the above described dimensions can treat a slurry only at the rate of about 400 L/day if the circulation conditions of the slurry are the same. On the contrary, the reactor 12 of the present embodiment can treat a slurry at the rate of about 40000 L/day (i.e., 28 L/min) in a large plant. Further, when the slurry is treated at the rate of about 40000 L/day, for example, a modified xylopolysaccharide is produced at the rate of about 1800 kg/day (Note: conventionally about 18 kg/day).

Further, in the plate member 16a, a hollowed part 16b (i.e., through hole) is formed so that the slurry can pass therethrough in the circumferential direction of the shaft 19. The formation of the hollowed part 16b enables formation of mild and complicated passages inside the reactor 12, allowing generation of plug-flow without disturbing the flow of the slurry, resulting in a more increase in the yield.

A shape and a size of the hollowed part 16b formed in the plate member 16a are not specifically limited. However, when the hollowed part 16b has a rectangular shape, a length (i.e., length in the flowing direction of slurry) of the hollowed part 16b may be, for example, in the range from 20 mm to 130 mm. Further, a height (i.e., length directed outward from the shaft 19) of the hollowed part 16b may be, for example, in the range from 30 mm to 200 mm.

Regarding a size of the passage controlling blade 16, a distance d (see FIG. 3A) between an inner wall of the pipe 11 and a peripheral part 16c of the passage controlling blade 16 is 5 mm or less in the present embodiment. This construction prevents sedimentation and retention of the slurry, allowing generation of more excellent plug-flow.

In the present embodiment, the reaction inside the reactor 12 is controlled by an index of the severity parameter in order to generate plug-flow inside the reactor 12. More specifically, the reaction temperature and time are controlled so that the severity parameter $R_0$ comes in the range from 3000 to 7000. Herein, the severity parameter $R_0$ is calculated by the following equation (1) under the conditions: at a temperature of 160° C. or more, at a pressure equal to or higher than a saturated vapor pressure at said temperature.

$$R_o = \int_0^t \exp\left(\frac{T(t) - T_r}{\omega}\right) dt \quad \text{Equation (1)}$$

where T(t) represents a time variation of a temperature (° C.); Tr represents a standard temperature (100° C.), t represents a time (min), and ω represents a constant (=14.75).

When the pressure is set to the saturated vapor pressure or higher and the temperature is set to 160° C. or more, a hydrothermal reaction is generated inside the reactor 12. Here, the severity parameter is a parameter obtained by converting the history data of the heat and time, which have imposed the slurry under the hydrothermal reaction condition of 100° C. or more, into an energy value. Hence, controlling the reaction by the severity parameter $R_0$ enables generation of the hydrothermal reaction under the precise reaction conditions so as to obtain a modified xylopolysaccharide.

A rotation rate of the shaft 19 arranged inside the reactor 12 is set such that the circumferential velocity of the periphery 16c of the passage controlling blade 16 is in the range from 0.02 m/sec to 0.3 m/sec. Setting the rotation rate of the periphery 16c to 0.02 m/sec or more may prevent the sedimentation and retention of a solid content of the slurry, and sufficiently suppress the side-reactions.

Alternatively, setting the rotation rate of the periphery 16c to 0.03 m/sec or less enables the plug-flow state to be sufficiently held, and prevents an under reaction caused by an abnormal passing and an excessive reaction due to retention of the slurry. This results in a sufficiently high yield. Moreover, setting the rotation rate of the shaft 19 in the above range may elongate a migration pathway of the slurry. This elongation may prevent an abnormal passing and sedimentation of the slurry as well as excessive retention. In addition, the result in increasing the heat conduction area may improve the heat conduction efficiency, allowing a compact design of the reactor 12.

Figure 4B:
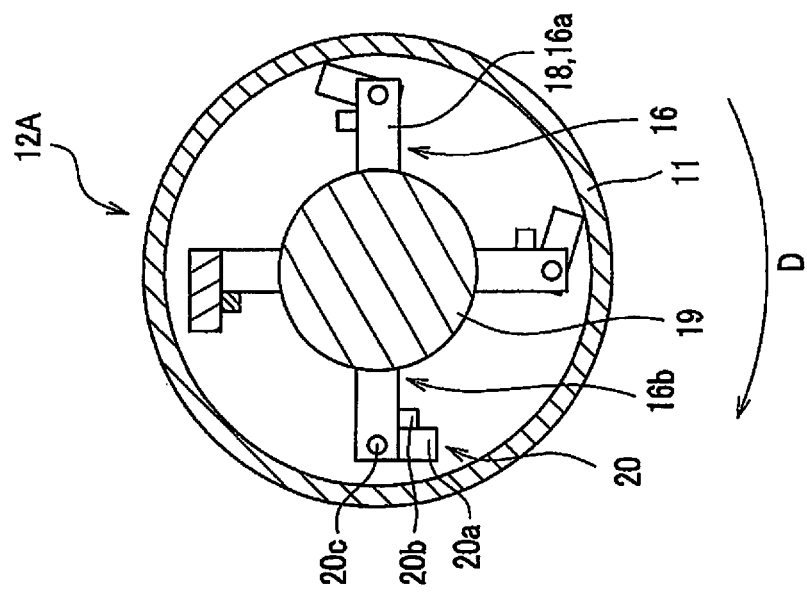
FIGS. 4A and 4B are diagrams showing inner structures of the reactor arranged in the reaction system of the present embodiment. They are modifications shown in FIGS. 3A and 3B.
Figure 4A:
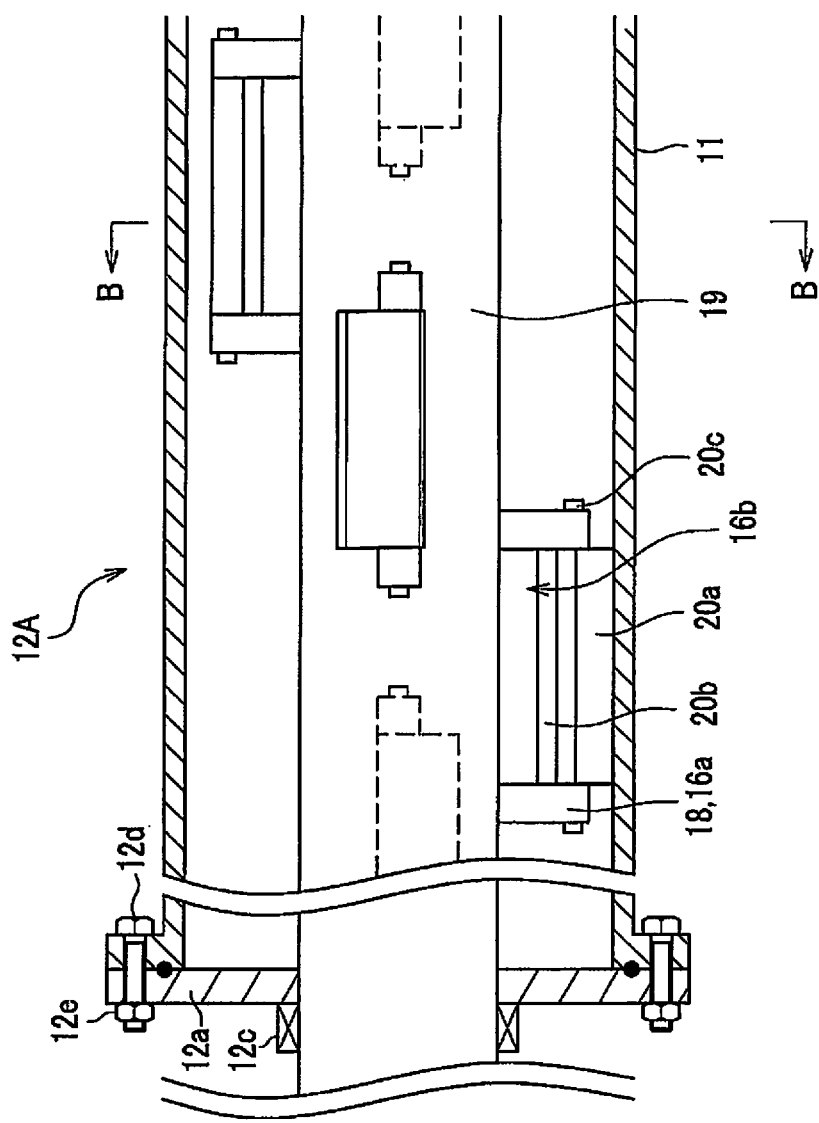

FIGS. 4A and 4B are diagrams showing the internal structure of a reactor 12A arranged in the reaction system 100 of a present embodiment. The reactor 12A is a modification of the reactor shown in FIGS. 3A and 3B. FIG. 4A is a cross-sectional diagram when viewed in the direction vertical to a flow of the slurry. FIG. 4B is a cross-sectional view taken along the line B-B of FIG. 4A. The reactor 12A shown in FIG. 4A includes a support 18, a scraping member 20a and a pressing member 20b.

The support 18 is a part of a plate member 16a to support the scraping member 20. The scraping member 20a is rotatably attached to the supports 18 which are arranged at peripheries of the plate members 16a (i.e., between the pair of supports 18) by bolts 20c. The pressing member 20b prevents the scraping member 20a from rotatably falling to the shaft 19 via gravitation. Note, the pressing member 20 forms a part of the plate member 16a. Further, a hollowed part 16b is formed between the pressing member 20b and the shaft 19.

In the reactor 12A, the scraping member 20a is driven as the shaft 19 is rotated. That is, as shown in FIG. 4B, the scraping member 20a located below the shaft 19 falls downward in the vertical direction so as to contact with the inner wall of the pipe 11. In this state, when the shaft 19 is rotated in the direction of the arrow D, rotation of the shaft 19 proceeds while the scraping member 20a contacts with the inner wall where the slurry is easily retained of the pipe 11. This mechanism prevents the slurry from being retained in the vicinity of the inner wall of the reactor 12, allowing highly accurate plug-flow to be generated without affected by a property of the slurry and a scale of the system.

<Comparative Investigation of Yields Between Batch Type Reactor and Reactor 12 of Present Embodiment>

(Investigation of Yield in Batch Type Reactor>

Next, modified xylopolysaccharides were produced by a batch type reactor (not shown) capable of precisely controlling a hydrothermal reaction, and a reactor 12 shown in FIGS. 3A and 3B for the purpose of investigating the effects of the reactors 12 and 12A capable of generating plug-flow.

First, a slurry was prepared so that ground materials of corncob meal (made in Thailand) had a solid content concentration of 13.0 mass %. Then, the resulting slurry (30 mL) was put into a SUS316 made batch type hydrothermal reactor (capacity of 50 mL, Taiatsu Techno). Next, the hydrothermal reaction was performed using salt baths at three temperature levels of 180° C., 190° C. and 200° C. for an optional reaction time ranging from 0 to 24 min, with a severity parameter $R_0$ ranging from 0 to 20000 calculated by the equation (1).

Specifically, the slurries were subjected to various severity parameters $R_0$s by selecting any temperature of 180° C., 190° C. and 200° C., and optionally changing the reaction time at the selected temperature. Note, the actual severity parameters imposed on the slurries were calculated by actually measuring temperature histories inside the hydrothermal reactor using a thermocouple during the hydrothermal reaction.

After completion of the hydrothermal reaction, the hydrothermal reactor itself was rapidly cooled by cold water, and products thus obtained were analyzed by HPLC. More specifically, contents of a modified xylopolysaccharide (i.e., including oligosaccharides with a degree of polymerization of 2 or more, ranging from about 2 to 12), xylose and furfural were measured with respect to soluble fractions of the slurry thus produced after the hydrothermal reaction.

Further, the amounts of the unreacted xylan were calculated based on the amounts of xylose thus produced by the sulfuric acid decomposition, with respect to the insoluble fractions of the slurry thus produced after the hydrothermal reaction. Moreover, as a theoretical approach, theoretical yields (i.e., production yield of each component when xylan was completely decomposed) of the modified xylopolysaccharide, xylose and furfural were calculated by the advanced analytical results of the saccharide composition of the corncob. Herein, the advanced analytical results had been obtained beforehand using an acidic hydrolytic decomposition method.

Figure 5:
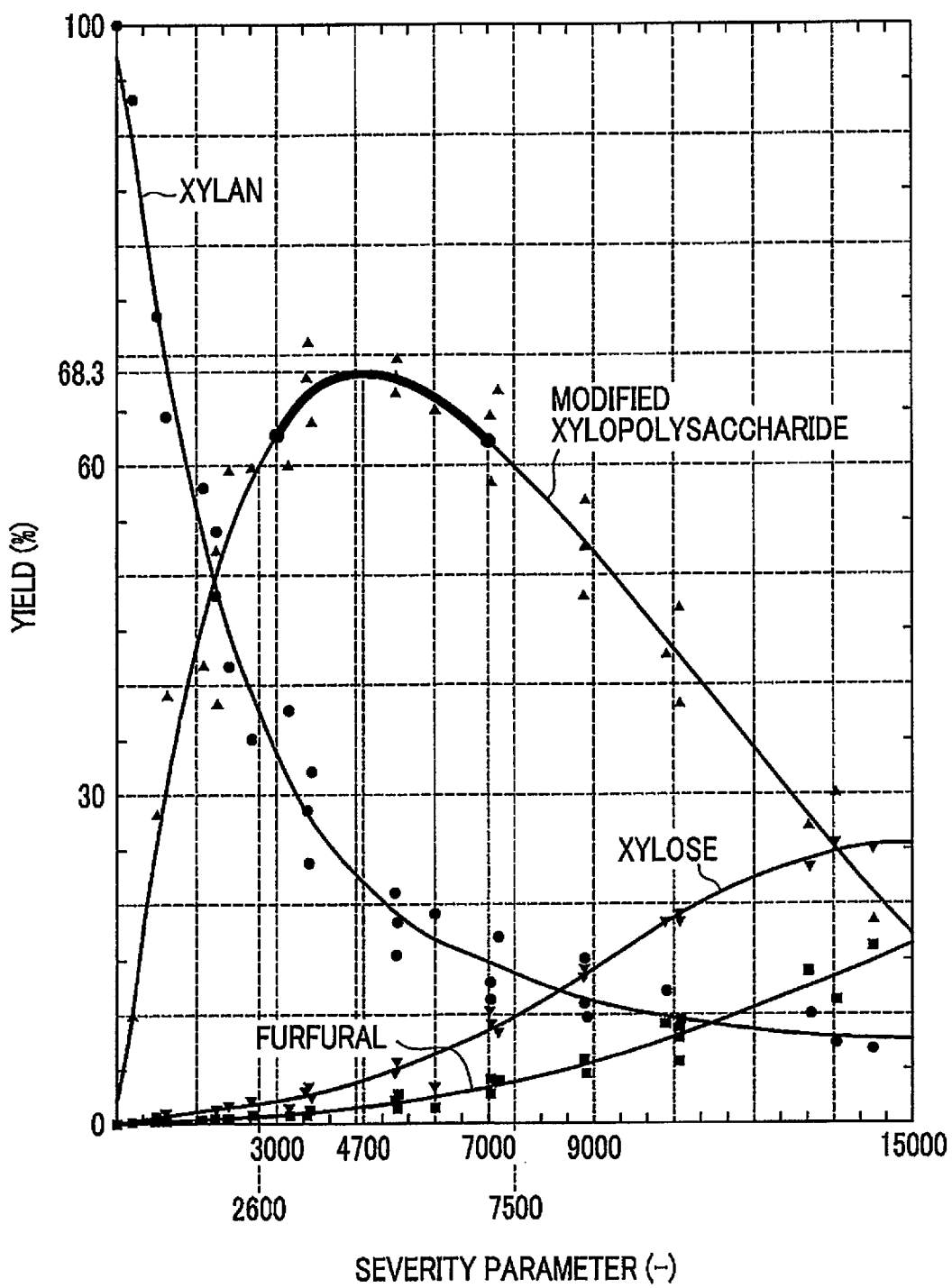
FIG. 5 is a graphic diagram showing yield curves of the products plotted against a severity parameter when a corncob material is subjected to an accurate hydrothermal reaction by a low-capacity batch type reactor that can precisely control the reaction conditions.

FIG. 5 is a graphic diagram showing yield curves of the products plotted against a severity parameter when a corncob material is subjected to an accurate hydrothermal reaction by a low-capacity batch type reactor that can precisely control the reaction conditions. A mark of ● represents a yield of xylan; a mark of ▲ represents a yield of the modified xylopolysaccharide; a mark of ▼ represents a yield of xylose; and a mark of ■ represents a yield of furfural, respectively. Here, approximating curves were drawn based on the plots of the respective components. The experimental equations of the respective components are the followings.

Xylan:

$$Y=2.77\times10^{-23}X^6-2.05\times10^{-18}X^5+6.16\times10^{-14}X^4-9.64\times10^{-10}X^3+8.42\times10^{-6}X^2-4.05\times10^{-2}X+1.00\times10^2$$

Modified Xylopolysaccharide:

$$Y=-1.95\times10^{-23}X^6+1.58\times10^{-18}X^5-5.16\times10^{-14}X^4+8.95\times10^{-10}X^3-8.80\times10^{-6}X^2+4.08\times10^{-2}X+6.25\times10^{-1}$$

Xylose:

$$Y=1.23\times10^{-19}X^5-5.99\times10^{-15}X^4+8.68\times10^{-11}X^3-3.29\times10^{-7}X^2+1.11\times10^{-3}X-1.01\times10^{-2}$$

Furfural:

$$Y=-3.10\times10^{-16}X^4+9.39\times10^{-12}X^3-1.24\times10^{-8}X^2+2.18\times10^{-4}X-5.53\times10^{-2}$$

Note: X represents a severity parameter and Y represents a yield, in the above equations.

Xylan is gradually hydrolyzed following an increase in the severity parameter, thereby yielding the modified xylopolysaccharide and xylose, and further furfural that is an excessive hydrolysate of xylose. When the severity parameter exceeds 2600, a theoretical yield of the modified polysaccharide exceeds 60%, and the yield shows a maximum value of 68.3% around the severity parameter of 4700. Then, as the severity parameter further increases, the modified xylopolysaccharide is further hydrolytically decomposed, resulting in a decrease in the yield. Eventually, as the severity parameter exceeds 7500, the yield again falls below 60% and simultaneously concentrations of xylose and furfural are increased.

As shown in FIG. 5, it was determined that the relationship between the severity parameter of the hydrothermal reaction and the yield of each component was extremely high regardless of the preset reaction temperatures. That is, although a temperature and a time were optionally set when controlling a severity parameter $R_0$, such a high relationship was obtained when plotting the yields against the severity parameters instead of the temperatures and times. Here, yields of xylose and furfural were sufficiently suppressed when the severity parameter was in the range from 3000 to 7000 as indicated by the medium thickness line. Further, in that range, the modified xylopolysaccharide was collected in a high yield.

Although it was not shown, similarly to the above analysis, yields obtained by a conventional tube type reactor were plotted. As a result, the yield curves were identical to those of FIG. 5 in the range from 3000 to 7000 of the severity parameter. Note, the conventional tube type reactor was disclosed in JP2008-253861 described hereinbefore; ϕ 25 mm, heat riser length: 8 m, heat riser capacity: 4000 mL, reactor length: 4 m, capacity: 2000 mL, standard treating rate: 300 mL/min (variable).

(Investigation of Yields in Reactor 12 of Present Embodiment)

Next, a hydrothermal reaction was tested using corncob meal (made in Thailand) in the reaction system provided with the reactor 12 shown in FIGS. 3A and 3B. in the reactor 12, the pipe 11 had an internal diameter of ϕ 140 mm, a length of 2200 mm (length in the direction of slurry flow), and the shaft 19 had a diameter of ϕ 62 mm. Further, the passage controlling blade 16 had a thickness of 10 mm (thickness in the direction vertical to the slurry flow).

Here, in the passage controlling blade 16, a rectangular hollowed part 16b was formed as shown in FIGS. 3A and 3B. The hollowed part 16b had the following dimensions: a width of 200 mm (length in the direction of the slurry flow), a height of 40 mm (length directed outward from the shaft 19), and a thickness of 10 mm. Further, the passage controlling blade 16 had a distance of 2 mm, between the periphery 16c and the internal wall of the pipe 11. The above dimensions provided the reactor 12 with an effective capacity of 24 L.

A corncob was ground by a ball mill so that a mean particle diameter was in the range from 30 μm to 60 μm measured by the above described analyzer. Warm water was added to the ground material to prepare a slurry type starting material. A temperature and a pump flow rate of the heater 17 in the reactor 12 were adjusted so as to set the reaction temperature ranging from 180° C. to 200° C., and the retention time inside the reactor 12 ranging from 9 min to 17 min.

Then, as a slurry to be fed, a corncob slurry with a solid content of 15.7 mass % to 18.6 mass % was made to pass through the reactor 12, and the reaction progress was observed. The slurry was made to pass therethrough at the flow rate of 2.4 ton to 4.5 ton per day (i.e., as a flow speed of 2 L/min).

In the reactor 12, a rotation rate of the shaft 19 was adjusted to 10 rpm (i.e., 0.07 m/s as the circumferential velocity of the periphery 16c in the passage controlling blade 16). As a result, the actual temperature inside the reactor 12 was precisely controlled within +2° C. relative to the prescribed temperature set to the reactor 12 in the temperature range where a hydrothermal reaction at 160° C. or higher was conducted. Further, a pressure inside the reactor 12 was stabilized at 2.0 Mpa that was above the vapor pressure.

A severity parameter of the slurry discharged from the material discharging tank 23 arranged at a downstream of the reactor 12 was calculated based on the temperature and flow rate (or time) inside the reactor 12 in operation. Then, yields per the severity parameters were plotted similarly to the yield curves in FIG. 5.

Figure 6:
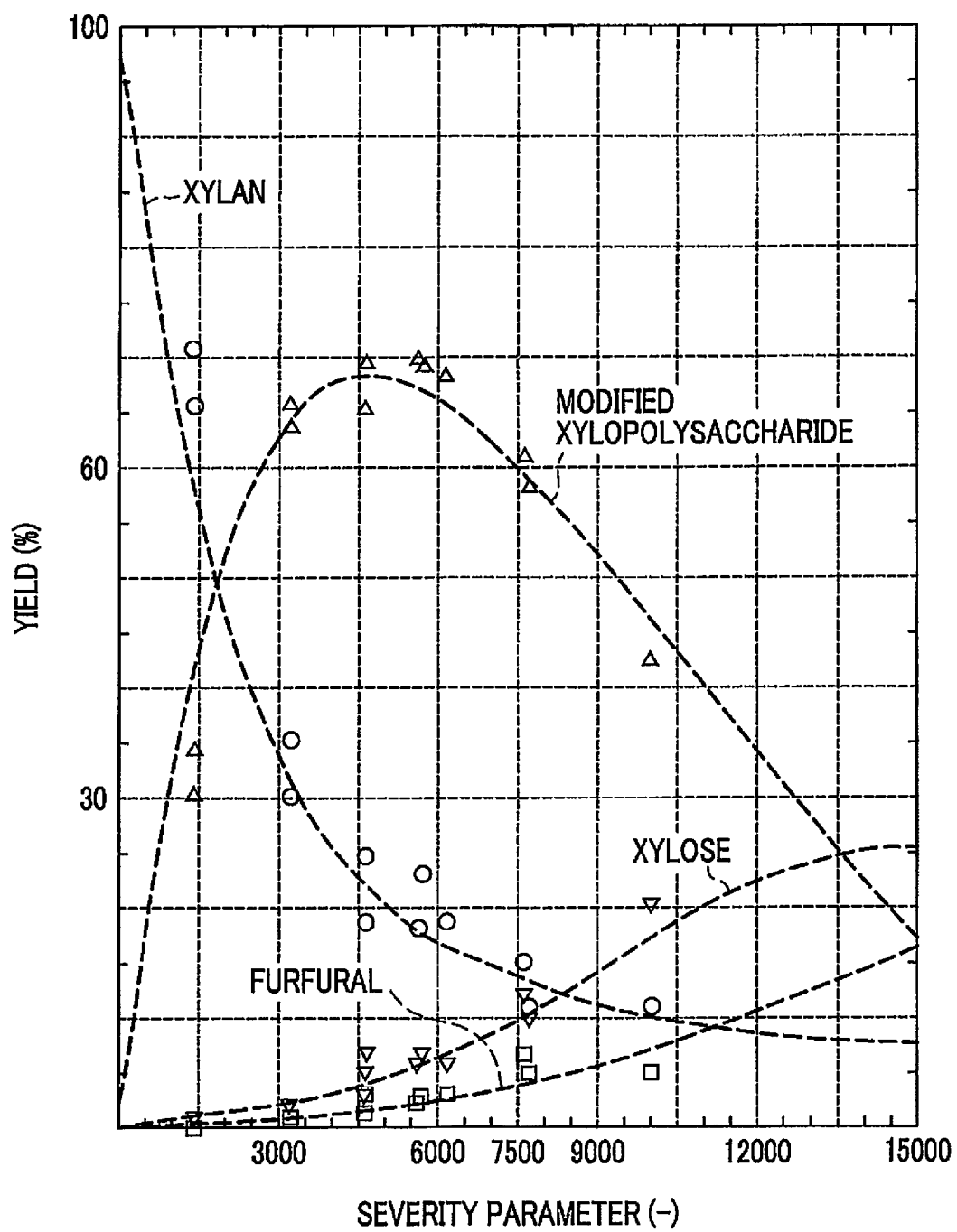
FIG. 6 is a graphic diagram showing comparison of yields when a corncob material is subjected to a hydrothermal reaction by the reactor of the present embodiment to yield curves accurately obtained by the batch type reactor.

FIG. 6 is a graphic diagram showing comparison of yields when a corncob material is subjected to a hydrothermal reaction in the reactor of the present embodiment to yield curves accurately obtained in the batch type reactor. A mark of ○ represents a yield of xylan; a mark of Δ represents a yield of the modified xylopolysaccharide; a mark of ∇ represents a yield of xylose; and a mark of □ represents a yield of furfural, respectively. Here, graphs shown by broken lines in FIG. 6 are equal to the yield curves shown by solid lines in FIG. 5.

As shown in FIG. 6, the respective yields of the modified xylopolysaccharide, xylose and furfural obtained by the collecting system 100 provided with the reactor 12 of the present embodiment were identical to the yield curves accurately obtained by the batch type reactor shown in FIG. 5. Particularly, those respective yields were precisely identical to the yield curves in the region with a severity parameter ranging from about 3000 to 7500.

The results of FIG. 6 demonstrate that the conditions of the hydrothermal reaction are sufficiently controlled in the continuous type reactor 12 having a scale of 2000 mL/min (i.e., pilot scale), similarly to the batch type reactor of 30 mL that can precisely control the hydrothermal reaction. Specifically, a total yield of the modified xylopolysaccharide and xylose is secured, suggesting that heat used for hydrolytically decomposing xylan was favorably conducted. Namely, it is suggested that heat is uniformly conducted also in the reactor 12 of the present embodiment, similarly to the batch type reactor precisely controlling a temperature. Therefore, it is considered that plug-flow is generated inside the reactor 12.

Further, the yield of the modified xylopolysaccharide shows the same tendency as the yield curve of the batch type reactor, as indicated by a broken line. The above finding suggests that small are a quantity of the slurry that passes through the reactor to remains as unreacted, a conversion rate to furfural, and a quantity of the slurry that retains in the reactor 12 for a long time. Those findings demonstrate that the reactor 12 generating plug-flow of the present embodiment can produce the modified xylopolysaccharide in a large scale, which has been difficult to be achieved in the conventional technology.

<Investigation on Structure of Modified Xylopolysaccharide Produced by Reactor 12>

Next, a structure of the modified xylopolysaccharide contained in the filtrate (i.e., soluble fraction) obtained by the collecting system 100 provided with the reactor 12 of the present embodiment was analyzed by HPLC and MALDI-TOF MA.

First, a slurry of the biomass containing xylan was subjected to the hydrothermal reaction under the condition with a severity parameter of 4600 by the reactor 12 shown in FIGS. 3A and 3B. Then, the resulting slurry thus discharged from the material discharging tank 23 located at a downstream of the reactor 12 (i.e., slurry produced after the hydrothermal reaction) was subjected to the centrifugal separation and filtration so as to remove an insoluble solid content, thereby to produce filtrate (soluble fraction). Next, the filtrate thus obtained was boiled for 3 hr in the presence of 1M sulfuric acid, and neutralized by a saturated aqueous solution of barium hydroxide. After removing insoluble barium sulfate, contents of monosaccharides and uronic acid were analyzed respectively by HPLC with an RI detector.

Further, contents of acetic acid and methanol respectively derivatised from acetyl and methyl groups were similarly analyzed respectively. Then, contents of the acetyl group and the methyl group were calculated based on the contents of acetic acid and methanol thus analyzed.

Moreover, contents of esterified ferulic acid and p-coumaric acid were determined by HPLC with a UV detector after those acid esters were subjected to a deesterification reaction at 65° C. for 2 hr under the alkaline condition of 1M sodium hydroxide aqueous solution, and neutralized by hydrochloric acid. Then, contents of ferulic acid and p-coumaric acid were calculated based on the contents of the esterified ferulic acid and p-coumaric acid thus analyzed as mentioned above.

The results of the analyses are shown in Table 1.

TABLE 1

| | | content | | substitution |
|---|---|---|---|---|
| | | (mg/g) | (mmol/g) | degree |
| mono- | xylose | 535 | 3561 | — |
| saccharides | glucose | 121 | 672 | — |
| | arabinose | 23 | 153 | 0.043 |
| | mannose | 19 | 104 | — |
| | galactose | 18 | 98 | — |
| substituents | acetyl group | 39 | 645 | 0.18 |
| | methyl group | 0 | 0 | — |
| | feruloyl group | 14 | 73 | 0.02 |
| | p-coumaroyl group | 4 | 26 | 0.0072 |

As shown in Table 1, xylose was detected as a main component. The detection of xylose was caused by acidic hydrolysis of the modified xylopolysaccharide that was soluble and produced through the hydrothermal reaction of xylan. The acidic hydrolysis of the modified xylopolysaccharide produced monomeric xylose included in the modified xylopolysaccharide. Further, the monosaccharides thus detected contained glucose, arabinose, mannose and galactose.

Further, an acetyl group, a feruloyl group and p-coumaroyl group were detected. Those results lead to the finding that the above substituents which have been detected only by a small scale hydrothermal reaction are well preserved in the pilot scale hydrothermal reaction performed by the reactor 12.

Further, a substitution degree represented by a mole ratio calculated based on the content of the acetyl group against the content of xylose was calculated. As a result, the substation degree was calculated as 0.18. The result indicates that 1 molecule of xylose is substituted with 0.18 moieties (about 2 moieties) of the acetyl groups. Thus, it is demonstrated that one acetyl group exists per xylopyranose having five linear-chains.

Similarly, also calculated were substitution degrees represented by the mole ratios calculated based on the contents of the arabinose group, the feruloyl group and the p-coumaroyl group respectively against the content of xylose. Accordingly, the substation degrees were calculated as 0.043, 0.02 and 0.0072, respectively. The results indicate that a feruloylarabinofuranosyl group and a coumaroylarabinofuranosyl group both of which exist only in xylan derived from plant cell walls are also preserved in the modified xylopolysaccharide thus obtained by the reactor 12.

<Investigation of Products when Modified Xylopolysaccharide Obtained by Reactor 12 is Subjected to Enzymatic Reaction>

The filtrate (130 mL; soluble fraction) used for obtaining the results in Table 1 was collected. Then, ethanol was slowly added to the collected filtrate while being slowly stirred until the ethanol concentration reached 80 vol %. After stood overnight at 4° C., precipitates were collected by glass filter. Then, the collected precipitates were washed with ethanol and acetone two times respectively, and the resulting products were dried in vacuo for 4 days.

About 3 g of the modified xylopolysaccharide was obtained from a solid thus subjected to the vacuum drying. Note, the resulting modified xylopolysaccharide was obtained by the reactor of the present embodiment. Then, the modified xylopolysaccharide was dissolved in ion-exchanged water with a pH value of 5 to 6 so as to prepare a modified xylopolysaccharide aqueous solution (1 mass %). The aqueous solution thus prepared was subjected to an enzymatic reaction test and a MALDI-TOF MS analysis.

The enzymes used for the enzymatic reaction test are derived from Streptomyces olivaceoviridis. Here, the enzymes thus used are 3 types consisting of purified β-xylosidase, and 2 types of purified endo-β-1,4-xylanase. The purified β-xylosidase is classified in GH43 of a glycoside hydrolase (GH) registered in the database of carbohydrate related enzyme (CAZ). The 2 types of purified endo-β-1,4-xylanase are classified in GH10 and GH 11 registered in the above described database. Those enzymes are purified so that the content of esterase is extremely limited.

Then, the 3 types of enzymes were added to the modified xylopolysaccharide aqueous solution (1 mass %) respectively so that each ratio (i.e., volume ratio) of the enzymes became 1 per 40 of the aqueous solution thus prepared. Next, the resulting solutions were subjected to the enzymatic reactions at 37° C. for 15 hr, respectively. After completion of the respective reactions, each solution was subjected to the thermal deactivation treatment at 100° C. for 5.0 min, and the resulting test solution was analyzed by MALDI-TOF MS.

In the analysis of MS spectra, detected were peaks corresponding to the modified xylopolysaccharides that were modified by mono-, di-, tri-, and tetra-acetyl groups (i.e., Ac1-Ac4) with a degree of polymerization of 4-12 or more, with respect to the modified xylopolysaccharide that was a substrate before subjected to the enzymatic reaction (FAXy13).

Figure 7:
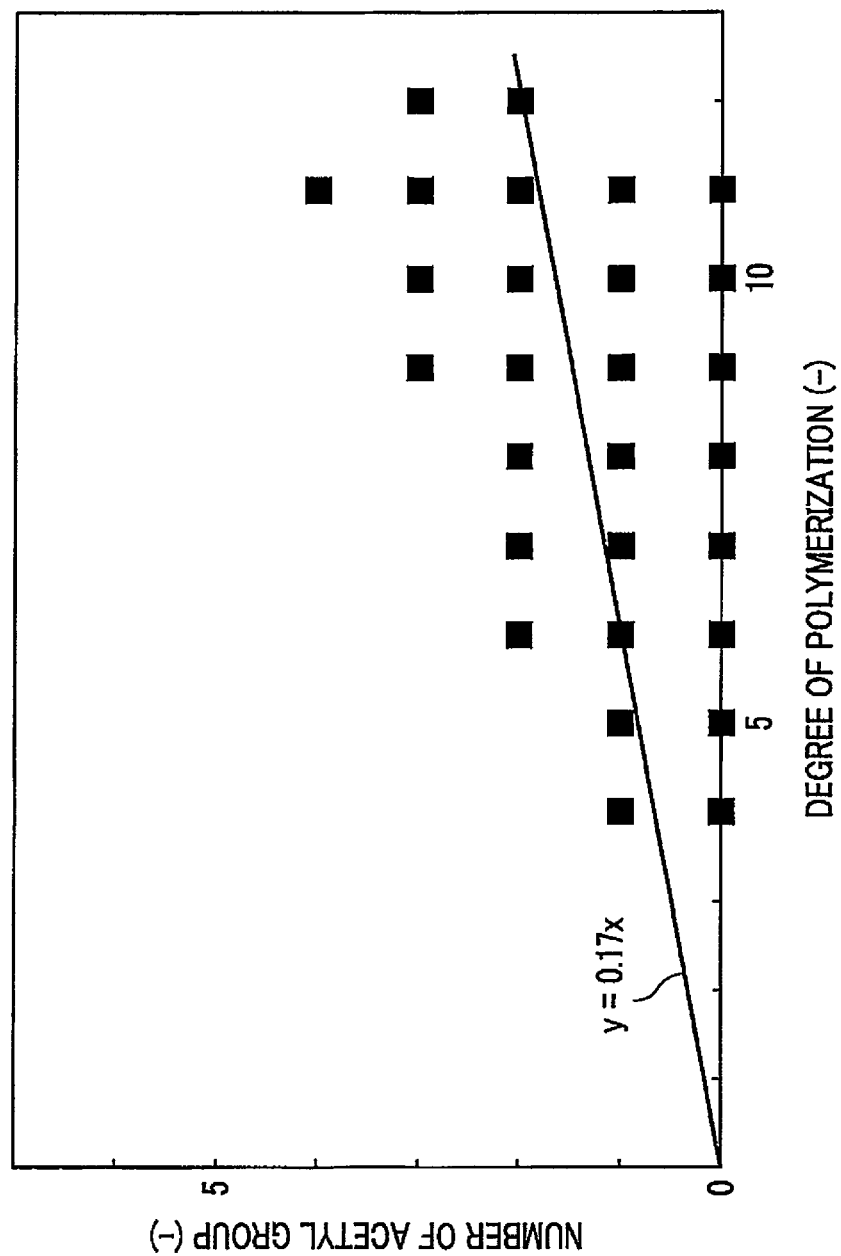
FIG. 7 shows MALDI-TOF MS analytical results of the relationships between a degree of polymerization and the number of acetyl group of the modified xylopolysaccharide produced by the reactor of the present embodiment.

FIG. 7 shows MALDI-TOF MS analytical results of the relationship between a degree of polymerization and the number of acetyl group of the modified xylopolysaccharide produced by the reactor 12 of the present embodiment. The relationship between a degree of polymerization and the number of acetyl group of the modified xylopolysaccharide was approximated by the experimental equation: $Y=0.17X$ (i.e., X represented a degree of polymerization, Y represented the number of acetyl group, and those definitions were the same as in FIGS. 8-10 as mentioned later).

The coefficient of 0.17 shown in the experimental equation represents a substitution degree of the acetyl group per monomeric xylose Here, the value was almost identical to the substitution degree of 0.18 obtained in the HPLC saccharide analysis in Table 1. The data indicates that the same results were obtained when the substitution degrees of the acetyl group were evaluated even by the completely different methods.

The result shows when the hydrothermal reaction is performed by the reactor 12 of the present embodiment, the acetyl groups which are substituents present in the xylan derived from plant cell walls are well preserved.

Figure 8:
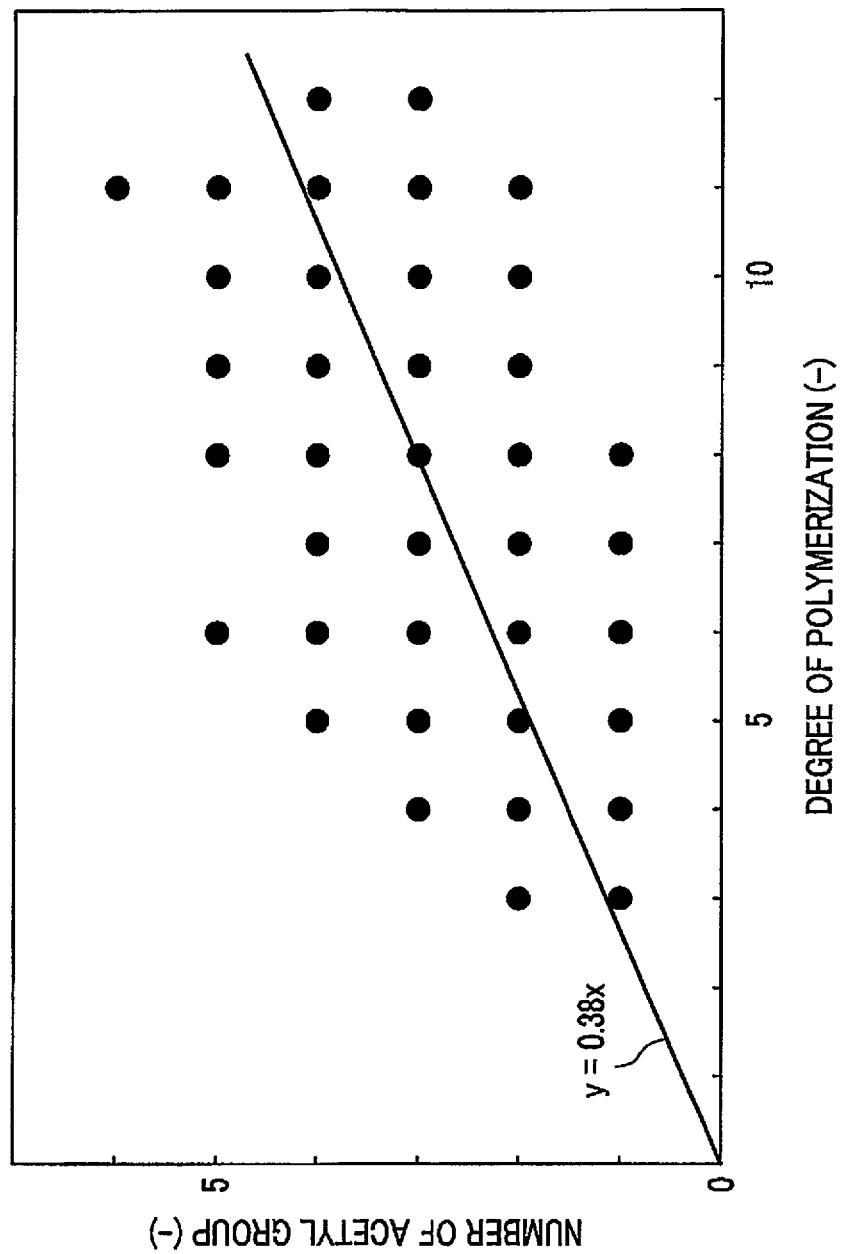
FIG. 8 shows MALDI-TOF MS analytical results of the relationship between a degree of polymerization and the number of acetyl group of the modified xylopolysaccharide produced by having β-xylosidase (GH43) act on the modified xylopolysaccharide produced by the reactor of the present embodiment.

FIG. 8 shows MALDI-TOF MS analytical results of the relationship between a degree of polymerization and the number of acetyl group of the modified xylooligosaccharide produced by applying β-xylosidase (GH43) to the modified xylopolysaccharide produced by the reactor 12 of the present embodiment. The relationship between a degree of polymerization and the number of acetyl group of the modified xylooligosaccharide was approximated by the experimental equation: $Y=0.38X$.

Here, β-xylosidase has a function for cutting out a xylosaccharide chain having no acetyl group from the nonreducing terminal side of xylan, whereby it is likely that the non-acetylated xylooligosaccharide chain is completely collected. On the other hand, the substitution degree of the acetyl groups of the remaining modified xylooligosaccharide is assumed to be 0.38 that is a slope of the approximated experimental equation. Accordingly, the substitution degree was larger than the number of acetyl group (0.18) of the original modified xylopolysaccharide shown in FIG. 7.

Here, it should be noted that the enzymatic reaction of β-xylosidase is inhibited by the modification of the acetyl groups and so on, and therefore β-xylosidase cannot cut a glycoside bond of the modified xylopolysaccharide. Hence, this reaction inhibition can be used for preventing the cleavage of the glycoside bond, allowing a highly acetylated xylooligosaccharide to be collected.

Further, it is assumed that an increase in the modified xylooligosaccharide with a larger degree of polymerization than the original modified xylopolysaccharide results from the presence of a macromolecular acetylated modified xylopolysaccharide with a degree of polymerization of 12 or more and not detected by MS, in the substrate (i.e., modified xylopolysaccharide before subjected to the enzymatic reaction). Namely, such a macromolecular acetylated modified xylopolysaccharide is hydrolytically decomposed into low molecules by the enzymatic reaction. Hence, it is assumed that this hydrolytic decomposition increases the concentration of the acetylated xylooligosaccharide thus detected.

Figure 9:
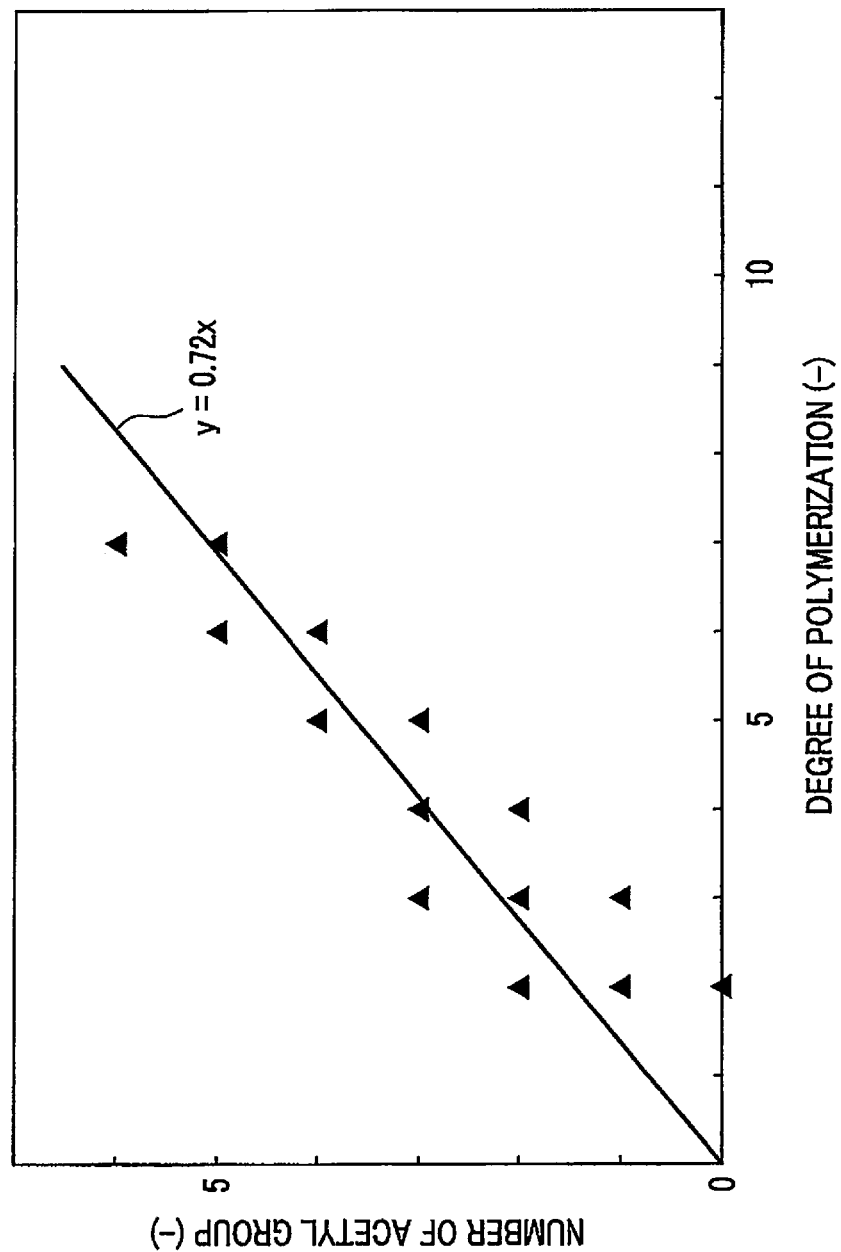
FIG. 9 shows MALDI-TOF MS analytical results of the relationships between a degree of polymerization and the number of acetyl group of the modified xylopolysaccharide produced by having endo-β-1,4-xylanase (GH10) act on the modified xylopolysaccharide produced by the reactor of the present embodiment.

FIG. 9 shows MALDI-TOF MS analytical results of the relationship between a degree of polymerization and the number of acetyl group of the modified xylopolysaccharide produced by applying β-1,4-xylanase (GH10) to the modified xylopolysaccharide produced by the reactor 12 of the present embodiment.

Figure 10:
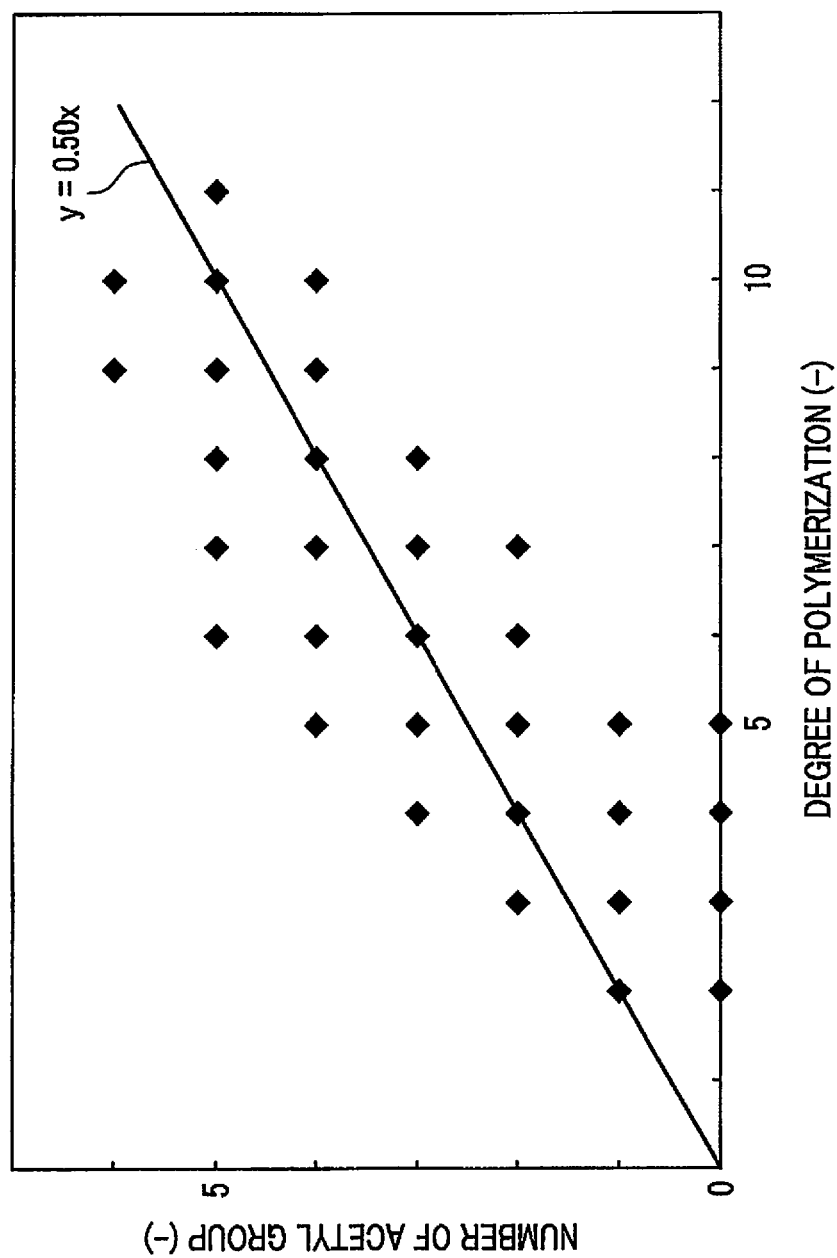
FIG. 10 shows MALDI-TOF MS analytical results of the relationships between a degree of polymerization and the number of acetyl group of the modified xylopolysaccharide produced by having endo-β-1,4-xylanase (GH11) act on the modified xylopolysaccharide.

Further, FIG. 10 shows MALDI-TOF MS analytical results of the relationship between a degree of polymerization and the number of acetyl group of the modified xylooligosaccharide produced by applying β-1,4-xylanase (GH11) to the modified xylopolysaccharide.

As shown in FIGS. 9 and 10, the number of acetyl group of the modified xylooligosaccharide was increased when either enzyme was used. More specifically, when β-xylosidase (GH10) was used (see FIG. 9), the number of acetyl group (i.e., a slope of approximate equation) was 0.72. When β-xylosidase (GH11) was used (see FIG. 10), the number of acetyl group (i.e., a slope of approximate equation) was 0.50. It is assumed that when β-xylosidase (GH10) is used among those enzymes, β-xylosidase (GH10) has high activity in the non-acetylated area, while the reaction is largely inhibited by the acetyl residue. Therefore, when compared to the latter (i.e., β-xylosidase (GH11)), the modified xylooligosaccharide having a low degree of polymerization and the large number of acetyl group can be collected.

In contrast, the modified xylopolysaccharide obtained by the reactor 12 of the present embodiment was subjected to the enzymatic decomposition via β-xylosidase (GH10) and β-xylosidase (GH11). The solutions thus obtained were analyzed by MAIDI-TOF MS. Table 2 summarizes the results. Table 2 lists types of the modified xylooligosaccharides obtained by the enzymatic reactions, and m/z values thereof.

TABLE 2

| Applied Enzymes | | | m/z |
| --- | --- | --- | --- |
| Xylosidases | Xylanases (GH10) | Xylanases (GH11) | ([M + Na]$^+$) |
| FAXyl2 | FAXYL2 | — | 614 |
| — | FAXyl2Ac1 | — | 656 |
| — | FAXyl2Ac2 | — | 698 |
| FAXyl3 | FAXyl3 | FAXyl3 | 745 |
| FAXyl3Ac1 | FAXyl3Ac1 | FAXyl3Ac1 | 788 |
| — | FAXyl3Ac2 | FAXyl3Ac2 | 830 |
| FAXyl4 | FAXyl4 | FAXyl4 | 878 |
| — | FAXyl4Ac1 | FAXyl4Ac1 | 920 |
| — | FAXyl4Ac2 | FAXyl4Ac2 | 962 |
| — | FAXyl4Ac3 | — | 1004 |
| FAXyl5 | FAXyl5 | FAXyl5 | 1010 |
| FAXyl5Ac1 | FAXyl5Ac1 | FAXyl5Ac1 | 1052 |
| — | FAXyl5Ac2 | — | 1094 |
| — | FAXyl6 | FAXyl6 | 1142 |
| — | — | FAXyl6Ac1 | 1184 |
| — | — | FAXyl6Ac2 | 1226 |
| — | — | FAXyl7Ac1 | 1316 |
| — | CAXyl2 | — | 583 |
| — | CAXyl2Ac1 | — | 626 |
| — | CAXyl3 | CAXyl3 | 716 |
| — | CAXyl3Ac1 | CAXyl3Ac1 | 758 |
| — | CAXyl4 | CAXyl4 | 848 |
| — | — | CAXyl4Ac1 | 890 |

In Table 2, "FA" represents a functional group of "feruloyl-α-L-arabinofuranosyl". "CA" represents "p-coumaroyl-α-L-arabinofuranosyl." Further, the number following "Xyl" represents the number of xyloses. For example, "FAXy13" represents "feruloyl-α-arabinofuranosyl-xylotriose." Moreover, "Ac" represents an acetyl group, and the number following "Ac" represents the number of the acetyl groups. Therefore, "FAXy13Ac1" represents "feruloyl-α-L-arabinofuranosyl-monoacetyl-xylotriose."

Furthermore, all of FAXy11, FAXy12, FAXy13, FaXy14, FAXy15, CAXy11, FAXy112, FAXy113 and FAXy114 are a kind of the modified xylopolysaccharides. This definition is similar to other saccharides.

The analytical results by MALDI-TOF MS demonstrated the detection of feruloyl-α-L-arabinofuranosyl-xylooligosaccharide (FA-xylooligosaccharide); and monoacetyl-FA-xylooligosaccharide, diacetyl-FA-xylooligosaccharide and triacetyl-FA-xylooligosaccharide, all of which were derived from FA-xylooligosaccharide bonded with 1-3 acetyl groups. As mentioned above, collected were various types oligosaccharide components derived from FA-xylopolysaccharides with the degree of polymerization of 2-7, to which 1-3 acetyl groups were bonded.

Specifically, FAXy12Ac1, FAXy12Ac2, FAXy12Ac3, FAXy13Ac1, FAXy13Ac2, FAXy13Ac3, FAXy14Ac1, FAXy14Ac2, FAXy14Ac3, FAXy15Ac1, FAXy15Ac2, FAXy15Ac3, FAXy16Ac1, FAXy16Ac2, FAXy16Ac3, FAXy17Ac1, FAXy17Ac2, and FAXy17Ac3 were collected.

Further, similarly to the above, the analytical results by MALDI-TOF MS demonstrated that the peaks of p-coumaroyl-α-L-arabinofuranosyl-xylooligosaccharide (CA-xylooligosaccharide) and monoacetyl-CA-xylooligosaccharide were also detected. Specifically, CAXy12, CAXy13, CAXy14, CAXy12Ac1, CAXy13Ac1 and CAXy14Ac1 were detected. Accordingly, it is found that the enzymatic reactions (i.e., with β-xylosidase and xylanase) applied to the modified xylopolysaccharides thus obtained by the reactor of the present embodiment enable production of modified xylooligosaccharides with high modification degrees.

Herein, The enzymatic reactions can preserve the substituents on the side chains of xylan derived from plant cell wall. Moreover, although it is not shown in FIGS, it is assumed that monosaccharide xylose is also produced as the enzymatic reactions further proceed, in addition to the above modified xylooligosaccharides.

Specifically, for example, highly acetylated xylooligosaccharides (i.e., mono-, di-, tri-, tetra- and penta-acetyl-xylooligosaccharides), and monosaccharide xylose can be collected in a short reaction time. Further, for example, besides the highly acetylated xylooligosaccharides as well as FA-xylooligosaccharide and CA-xylooligosaccharide, modified xylooligosaccharides such as mono-, di- or tri-acetyl-FA-XOS and mono-, di- or tri-acetyl CA-XOS can be also collected.

As mentioned hereinbefore, the use of the reactor 12 that generates plug-flow, and the control of the severity parameter can produce the modified xylopolysaccharides preserving the substituents on the side chains thereof. The modified xylopolysaccharides thus obtained are easily subjected to the enzymatic reaction since they have been solubilized.

Therefore, when a small amount of the purified enzyme is used to those modified xylopolysaccharides, the enzymatic reaction rapidly proceeds, allowing the large amounts and low costs production of the modified xylooligosaccharides with a high modification degree and usability such as FAXy12Ac1.

SUMMARY

As mentioned hereinbefore, the modified xylopolysaccharides thus obtained by the reactor 12 were polysaccharides ranging from oligosaccharides with a degree of polymerization of about 2-12 to polymers with a degree of polymerization of 20 or more. Further, large amounts of the modified xylopolysaccharides were collected while preserving the substituents such as an acetyl group, a feruloyl-α-L-arabinofuranosyl group (FA), and p-coumaroyl-α-L-arabinofuranosyl group (CA) of which large amounts were originally included in plant cell walls.

Meanwhile, although detailed explanations have been omitted, when the modified xylopolysaccharide thus produced by the hydrothermal reaction is made to react with β-xylosidase or endo-β-1,4-xylanase, the resulting reaction rate becomes about 24-fold to 48-fold higher than that of the reaction in which xylan-containing biomass is subjected to the enzymatic reaction after being subjected to an alkaline pre-treatment or a digestive pre-treatment.

Further, the conventional method for performing an alkaline treatment to biomass or performing an enzymatic treatment containing esterase allows the substituents such as an acetyl group to be completely removed. Thus, in the conventional method, the hydrolytic decomposition proceeds to produce a low molecular and non-modified homo-xylooligosaccharide. This makes it difficult to produce a modified hetero-xylooligosaccharide.

Moreover, when the severity parameter is low, the hydrolytic decomposition hardly proceeds, resulting in a decrease in the yield of the modified xylopolysaccharide. In contrast, when the severity parameter is high, not only the yield of the modified xylopolysaccharide is decreased but also the substituents tend to be easily removed, resulting in a decrease in the substituents of the modified xylopolysaccharide.

Namely, there is a relationship between the severity parameter affecting the xylan-containing biomass material during the hydrothermal reaction and the amount of the remaining substituents.

Hence, the reactor 12 generating plug-flow is used in the present embodiment in order to provide a uniform and desirable severity parameter with all of the raw materials. Thus, analyzing the preservation profile of the substituents of the modified xylopolysaccharide enables accurate estimation of the reaction history on what degree of the hydrothermal reaction was performed.

Further, if the slurry thus obtained by the reactor 12 of the present embodiment is purified via membrane separation, active carbon and ion-exchange treatments and subsequently concentrated, and further subjected to spray drying and freeze-drying, white powder containing the modified xylopolysaccharide is obtained. Here, the substituents are preserved on the side chains of the modified xylopolysaccharide. Thus, despite of whatever the modified xylopolysaccharide is a polymer, the water solubility thereof becomes high.

Moreover, the modified xylopolysaccharide is a stable saccharide having delicate sweetness derived from a low molecular xylopolysaccharide as well as soft and pleasant touch on the tongue like sugar.

A basic skeleton of the modified xylopolysaccharide is constructed by a β-1,4-bond of hemicellulose. Therefore, the modified xylopolysaccharide is considered as dietary fiber having water solubility, which affords a functionality of dietary fiber that is difficult to be taken in the present dietary lifestyle. Further, water soluble modified xylopolysaccharides which preserve the side chains are difficultly hydrolyzed in the pH environment inside the digestive organs. Eventually, most of the modified xylopolysaccharides reach inside the intestines in an intact form.

Those characteristics allow a part of the modified xylopolysaccharides having reached the intestines to be utilized by microorganism thereby to produce useful organic acids such as acetic acid, ferulic acid and coumaric acid. Accordingly, the modified xylopolysaccharides are expected to be utilized to an excellent prebiotics material.

DESCRIPTION OF REFERENCE NUMBERS

11 Pipe
12 Reactor
16 Passage Controlling Blade (i.e., Passage Controlling Mechanism)
16a Plate Member (i.e., Passage Controlling Mechanism)
16b Hollowed Part (or Through Hole; i.e., Passage Controlling Mechanism)
16c Peripheral Part (i.e., Passage Controlling Mechanism)
18 Support (i.e., Plate Member, Passage Controlling Mechanism)
19 Shaft (i.e., Rotator)
20a Scraping Member (i.e., Passage Controlling Mechanism)
20b Pressing Member (i.e., Passage Controlling Mechanism)
20c Bolt (i.e., Passage Controlling Mechanism)
100 Reaction System

The invention claimed is:
1. A method for producing a modified xylopolysaccharide,
the method comprising the steps of:
providing biomass as a raw material which comprises xylan in plant cell walls thereof, wherein the xylan comprises at least one of substituents selected from the group consisting of an acetyl group, a feruloylarabinofuranosyl group and a coumaroylarabinofuranosyl group on a side chain thereof;
preparing a slurry which contains the biomass in 10 mass % to 30 mass % as a solid content;
feeding the slurry into a cylindrical plug-flow reactor which comprises a passage controlling mechanism inside the reactor, wherein
the passage controlling mechanism generates a plug flow which is an extruded flow and makes the slurry flow with a distribution of equal velocities inside the reactor,
the passage controlling mechanism comprising
a columnar rotator that is rotatable around a center axis arranged in a direction parallel to a flow of the slurry, and
a plurality of passage controlling blades including a plate member which is arranged on a side surface of the rotator, directed outward the rotator and extended in a direction of the flow of the slurry; and
performing a continuous hydrothermal treatment to the slurry in the reactor to produce the modified xylopolysaccharide in which the substituent on the side chain of the xylan is preserved, wherein
the modified xylopolysaccharide has a theoretical yield of more than 60 percent, and
the continuous hydrothermal treatment is performed under controlled conditions: at a temperature of 160° C. or more, at a pressure equal to or higher than a saturated water vapor pressure at said temperature, and with a severity parameter $R_0$ ranging from 3000 to 7000 calculated by the following equation (1),

$$R_o = \int_0^\tau \exp\left(\frac{T(t) - T_r}{\omega}\right) dt$$

wherein T(t) is a time variation of a temperature (° C.), $T_r$ is a standard temperature (100° C.), t is a time (min) and ω is a constant (=14.75).

2. The method for producing a modified xylopolysaccharide described in claim 1, wherein a periphery of the passage controlling blade facing an inner wall of the plug-flow reactor has a distance of 5 mm or less from the inner wall.

3. The method for producing a modified xylopolysaccharide described in claim 1, wherein the rotator is rotated so that a circumferential velocity of a periphery of the plate member is in the range from 0.02 m/sec to 0.3 m/sec.

4. The method for producing a modified xylopolysaccharide described in claim 1, wherein a through hole is formed in the plate member so that the slurry passes therethrough in a circumferential direction of the rotator.

5. The method for producing a modified xylopolysaccharide described in claim 1, wherein
 a scraping member rotatable around the center axis at a periphery of the plate member is arranged, and
 the scraping member contacts with an inner wall of the plug-flow reactor as the rotator is rotated.

6. The method for producing a modified xylopolysaccharide described in claim 1,
 the method further comprising a step of reacting the modified xylopolysaccharide produced through the continuous hydrothermal treatment with at least either β-xylosidase or xylanase,
 so that the modified xylopolysaccharide decomposes to a specifically modified xylooligosaccharide in which the substituent on the side chain of the xylan is preserved.

\* \* \* \* \*